(12) United States Patent
Haarstad et al.

(10) Patent No.: US 7,494,460 B2
(45) Date of Patent: Feb. 24, 2009

(54) METHODS AND APPARATUS PROVIDING SUCTION-ASSISTED TISSUE ENGAGEMENT THROUGH A MINIMALLY INVASIVE INCISION

(75) Inventors: Philip J. Haarstad, Chanhassen, MN (US); Christopher P. Olig, Eden Prairie, MN (US); Paul T. Rothstein, Maple Grove, MN (US); Michael J. Hobday, Lino Lakes, MN (US); William J. Steinberg, Coon Rapids, MN (US); David J. S. Kim, Maple Grove, MN (US); Thomas P. Daigle, Corcoran, MN (US); Ann M. Thomas, Plymouth, MN (US); Brian J. Ross, Maple Grove, MN (US); Steven C. Christian, New Brighton, MN (US); Robert H. Reetz, Rockford, MN (US); Douglas H. Gubbin, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 753 days.

(21) Appl. No.: 10/675,815

(22) Filed: Sep. 30, 2003

(65) Prior Publication Data
US 2004/0138522 A1 Jul. 15, 2004

Related U.S. Application Data

(63) Continuation-in-part of application No. 10/643,299, filed on Aug. 19, 2003, now Pat. No. 7,338,434.

(60) Provisional application No. 60/404,969, filed on Aug. 21, 2002, provisional application No. 60/424,243, filed on Nov. 6, 2002.

(51) Int. Cl.
*A61F 2/00* (2006.01)

(52) U.S. Cl. .................................... 600/37

(58) Field of Classification Search ................ 128/897, 128/898; 600/37, 201–205, 208, 210, 235; 606/1, 108, 191, 158
See application file for complete search history.

(56) References Cited

U.S. PATENT DOCUMENTS

| 452,131 A | 5/1891 | Haughawout |
|---|---|---|
| 2,590,527 A | 3/1952 | Fluck |

(Continued)

FOREIGN PATENT DOCUMENTS

| EP | 0 167 345 A1 | 1/1986 |
|---|---|---|
| EP | 0 293 760 A3 | 5/1988 |

(Continued)

OTHER PUBLICATIONS

Kolessov V.I. The Surgery of Coronary Arteries of the Heart, Leningrad, Meditsina, 1977, pp. 360. (English Translation).

(Continued)

*Primary Examiner*—Samuel G Gilbert
(74) *Attorney, Agent, or Firm*—Mike Jaro; Jeffrey J. Hohenshell

(57) ABSTRACT

Suction-assisted tissue-engaging devices, systems, and methods are disclosed that can be employed through minimal surgical incisions to engage tissue during a medical procedure through application of suction to the tissue through a suction member applied to the tissue. A shaft is introduced into a body cavity through a first incision, and a suction head is attached to the shaft via a second incision. The suction head is applied against the tissue by manipulation of the shaft and suction is applied to engage the tissue while the medical procedure is performed through the second incision. A system coupled to the shaft and a fixed reference point stabilizes the shaft and suction head. When the medical procedure is completed, suction is discontinued, the suction head is detached from the shaft and withdrawn from the body cavity through the second incision, and the shaft is retracted through the first incision.

33 Claims, 16 Drawing Sheets

U.S. PATENT DOCUMENTS

| | | | |
|---|---|---|---|
| 3,577,982 A | 5/1971 | La Par | |
| 3,720,433 A | 3/1973 | Rosfelder | |
| 3,783,873 A | 1/1974 | Jacobs | |
| 3,786,815 A | 1/1974 | Ericson | |
| 3,858,926 A | 1/1975 | Ottenhues | |
| 3,916,909 A | 11/1975 | Kletschka et al. | |
| 3,951,138 A | 4/1976 | Akopov | |
| 3,983,863 A | 10/1976 | Janke et al. | |
| 3,999,795 A | 12/1976 | Barker | |
| 4,047,532 A | 9/1977 | Phillips et al. | |
| 4,049,000 A | 9/1977 | Williams | |
| 4,049,002 A | 9/1977 | Kletschka et al. | |
| 4,096,864 A | 6/1978 | Kletschka et al. | |
| 4,306,561 A | 12/1981 | De Medinaceli | |
| 4,314,568 A | 2/1982 | Loving | |
| 4,350,160 A | 9/1982 | Kolesov | |
| 4,366,819 A | 1/1983 | Kaster | |
| 4,368,736 A | 1/1983 | Kaster | |
| 4,428,368 A | 1/1984 | Torii | |
| 4,447,227 A | 5/1984 | Kotsanis | |
| 4,463,980 A | 8/1984 | Orii | |
| 4,627,421 A | 12/1986 | Symbas et al. | |
| 4,637,377 A | 1/1987 | Loop | |
| 4,646,747 A | 3/1987 | Lundbáck | |
| 4,688,570 A | 8/1987 | Kramer et al. | |
| 4,711,247 A | 12/1987 | Fishman | |
| 4,718,418 A | 1/1988 | L'Esperance, Jr. | |
| 4,726,356 A | 2/1988 | Santilli et al. | |
| 4,736,749 A | 4/1988 | Lundback | |
| 4,767,142 A | 8/1988 | Takahashi et al. | |
| 4,808,163 A | 2/1989 | Laub | |
| 4,852,552 A | 8/1989 | Chaux | |
| 4,854,318 A | 8/1989 | Solem et al. | |
| 4,865,019 A | 9/1989 | Phillips | |
| 4,892,343 A | 1/1990 | Hall | |
| 4,904,012 A | 2/1990 | Nishiguchi et al. | |
| 4,925,443 A | 5/1990 | Heilman et al. | |
| 4,955,896 A | 9/1990 | Freeman | |
| 4,962,758 A | 10/1990 | Lasner et al. | |
| 4,973,300 A | 11/1990 | Wright | |
| 4,989,587 A | 2/1991 | Farley | |
| 4,991,578 A | 2/1991 | Cohen | |
| 5,009,660 A | 4/1991 | Clapham | |
| 5,011,469 A | 4/1991 | Buckberg et al. | |
| 5,053,041 A | 10/1991 | Ansari et al. | |
| 5,098,369 A | 3/1992 | Heilman et al. | |
| 5,108,412 A | 4/1992 | Krumeich et al. | |
| 5,119,804 A | 6/1992 | Anstadt | |
| 5,131,905 A | 7/1992 | Grooters | |
| 5,133,737 A | 7/1992 | Grismer | |
| 5,167,223 A | 12/1992 | Koros et al. | |
| 5,171,254 A | 12/1992 | Sher | |
| 5,207,467 A | 5/1993 | Smith | |
| 5,256,132 A | 10/1993 | Snyders | |
| 5,287,861 A | 2/1994 | Wilk | |
| 5,290,082 A | 3/1994 | Palmer et al. | |
| 5,300,087 A | 4/1994 | Knoepfler | |
| 5,324,087 A | 6/1994 | Shimose et al. | |
| 5,336,252 A | 8/1994 | Cohen | |
| 5,365,921 A | 11/1994 | Bookwalter et al. | |
| 5,372,124 A | 12/1994 | Takayama et al. | |
| 5,374,277 A | 12/1994 | Hassler | |
| 5,383,840 A | 1/1995 | Heilman et al. | |
| 5,417,709 A | 5/1995 | Slater | |
| 5,425,705 A | 6/1995 | Evard et al. | |
| 5,437,651 A | 8/1995 | Todd et al. | |
| 5,452,733 A | 9/1995 | Sterman et al. | |
| 5,472,438 A | 12/1995 | Schmit et al. | |
| 5,503,617 A | 4/1996 | Jako | |
| 5,509,890 A | 4/1996 | Kazama | |
| 5,545,123 A | 8/1996 | Ortiz et al. | |
| 5,553,198 A | 9/1996 | Wang | |
| 5,556,147 A | 9/1996 | Somekh et al. | |
| 5,607,421 A | 3/1997 | Jeevanandam et al. | |
| 5,613,937 A | 3/1997 | Garrison et al. | |
| 5,657,429 A | 8/1997 | Wang | |
| 5,667,624 A | 9/1997 | Akimoto et al. | |
| 5,702,420 A | 12/1997 | Sterling et al. | |
| 5,727,569 A | 3/1998 | Benetti et al. | |
| 5,730,757 A | 3/1998 | Benetti et al. | |
| 5,735,290 A * | 4/1998 | Sterman et al. | 128/898 |
| 5,749,892 A | 5/1998 | Vierra et al. | |
| 5,772,583 A | 6/1998 | Wright et al. | |
| 5,782,746 A | 7/1998 | Wright | |
| 5,799,661 A | 9/1998 | Boyd et al. | |
| 5,807,243 A | 9/1998 | Vierra et al. | |
| 5,827,216 A | 10/1998 | Igo et al. | |
| 5,836,311 A | 11/1998 | Borst et al. | |
| 5,865,730 A | 2/1999 | Fox et al. | |
| 5,875,782 A | 3/1999 | Ferrari et al. | |
| 5,876,332 A | 3/1999 | Looney | |
| 5,885,271 A | 3/1999 | Hamilton et al. | |
| 5,888,247 A | 3/1999 | Benetti | |
| 5,891,017 A | 4/1999 | Swindle et al. | |
| 5,894,843 A | 4/1999 | Benetti et al. | |
| 5,906,607 A | 5/1999 | Taylor et al. | |
| 5,927,284 A | 7/1999 | Borst et al. | |
| 5,947,896 A | 9/1999 | Sherts et al. | |
| 5,957,835 A | 9/1999 | Anderson et al. | |
| 5,967,972 A | 10/1999 | Santilli et al. | |
| 5,976,080 A | 11/1999 | Farascioni | |
| 5,976,171 A | 11/1999 | Taylor | |
| 5,984,864 A | 11/1999 | Fox et al. | |
| 6,007,486 A | 12/1999 | Hunt et al. | |
| 6,015,378 A | 1/2000 | Borst et al. | |
| 6,017,304 A | 1/2000 | Vierra et al. | |
| 6,019,722 A | 2/2000 | Spence et al. | |
| 6,030,340 A | 2/2000 | Maffei et al. | |
| 6,032,672 A | 3/2000 | Taylor | |
| 6,033,362 A | 3/2000 | Cohn | |
| 6,036,641 A | 3/2000 | Taylor et al. | |
| 6,050,266 A | 4/2000 | Benetti et al. | |
| 6,063,021 A | 5/2000 | Hossain et al. | |
| 6,071,235 A | 6/2000 | Furnish et al. | |
| 6,071,295 A | 6/2000 | Takahashi | |
| 6,102,854 A | 8/2000 | Cartier et al. | |
| 6,110,187 A | 8/2000 | Donlon | |
| 6,113,534 A | 9/2000 | Koros et al. | |
| 6,139,492 A | 10/2000 | Vierra et al. | |
| 6,152,874 A | 11/2000 | Looney et al. | |
| 6,159,201 A | 12/2000 | Hamilton et al. | |
| 6,174,307 B1 | 1/2001 | Daniel et al. | |
| 6,210,323 B1 | 4/2001 | Gilhuly et al. | |
| 6,213,941 B1 | 4/2001 | Benetti et al. | |
| 6,238,334 B1 | 5/2001 | Easterbrook, III et al. | |
| 6,251,065 B1 | 6/2001 | Kochamba et al. | |
| 6,258,023 B1 | 7/2001 | Rogers et al. | |
| 6,328,688 B1 | 12/2001 | Borst | |
| 6,334,843 B1 | 1/2002 | Borst | |
| 6,336,898 B1 | 1/2002 | Borst | |
| 6,350,229 B1 | 2/2002 | Borst | |
| 6,364,826 B1 | 4/2002 | Borst | |
| 6,371,906 B1 | 4/2002 | Borst | |
| 6,371,910 B1 | 4/2002 | Zwart et al. | |
| 6,394,948 B1 | 5/2002 | Borst | |
| 6,394,951 B1 | 5/2002 | Taylor et al. | |
| 6,395,015 B1 | 5/2002 | Borst | |
| 6,459,926 B1 | 10/2002 | Nowlin et al. | |
| 6,464,629 B1 | 10/2002 | Boone et al. | |
| 6,464,630 B1 | 10/2002 | Borst | |
| 6,468,265 B1 | 10/2002 | Evans | |
| 6,488,618 B1 | 12/2002 | Paolitto et al. | |
| 6,503,245 B2 | 1/2003 | Palmer et al. | |
| 6,506,149 B2 | 1/2003 | Peng et al. | |

| | | |
|---|---|---|
| 6,511,416 B1 | 1/2003 | Green, II et al. |
| 6,517,563 B1 | 2/2003 | Paolitto et al. |
| 6,551,242 B1 | 4/2003 | Furnish et al. |
| 6,558,314 B1 | 5/2003 | Adelman et al. |
| 6,585,643 B2 | 7/2003 | Clem et al. |
| 6,589,166 B2 | 7/2003 | Knight et al. |
| 6,602,183 B1 | 8/2003 | Levi et al. |
| 6,602,189 B1 | 8/2003 | Bennetti et al. |
| 6,607,479 B1 | 8/2003 | Kochamba et al. |
| 6,740,028 B2 | 5/2004 | Boone et al. |
| 6,755,780 B2 | 6/2004 | Borst |
| 6,936,001 B1 | 8/2005 | Snow |
| 7,048,683 B2 | 5/2006 | Borst |
| 7,338,434 B1 | 3/2008 | Haarstad et al. |
| 2001/0041827 A1 | 11/2001 | Spence et al. |
| 2002/0045888 A1 | 4/2002 | Ramans |
| 2002/0082612 A1 | 6/2002 | Moll |
| 2002/0099268 A1 | 7/2002 | Paul et al. |
| 2002/0128552 A1 | 9/2002 | Nowlin |
| 2002/0137989 A1 | 9/2002 | Clem et al. |
| 2002/0161277 A1 | 10/2002 | Mansvelt-Beck et al. |
| 2002/0165434 A1 | 11/2002 | Williamson, IV et al. |
| 2003/0013949 A1 | 1/2003 | Moll |
| 2003/0055410 A1 | 3/2003 | Evans |
| 2003/0078470 A1 | 4/2003 | Borst |
| 2003/0078471 A1 | 4/2003 | Foley et al. |
| 2003/0083554 A1 | 5/2003 | Paolitto et al. |
| 2003/0088150 A1 | 5/2003 | Green, II et al. |
| 2003/0120268 A1 | 6/2003 | Bertolero et al. |
| 2003/0125604 A1 | 7/2003 | Kochamba et al. |
| 2003/0158463 A1 | 8/2003 | Julian et al. |
| 2003/0158464 A1 | 8/2003 | Bertolero |
| 2003/0216715 A1 | 11/2003 | Moll |
| 2004/0092875 A1 | 5/2004 | Kochamba |
| 2004/0102771 A1 | 5/2004 | Bertolero et al. |
| 2004/0167549 A1 | 8/2004 | Borst |
| 2004/0181118 A1 | 9/2004 | Kochamba |
| 2004/0181119 A1 | 9/2004 | Kochamba |
| 2004/0181120 A1 | 9/2004 | Kochamba |
| 2005/0010079 A1 | 1/2005 | Bertolero et al. |
| 2005/0033270 A1 | 2/2005 | Ramans |
| 2005/0059853 A9 | 3/2005 | Kochamba |
| 2005/0107808 A1 | 5/2005 | Evans |
| 2006/0025756 A1 | 2/2006 | Francischelli et al. |
| 2006/0036128 A1 | 2/2006 | Borst |
| 2006/0178559 A1 | 8/2006 | Kumar |
| 2006/0241414 A1 | 10/2006 | Nowlin |

FOREIGN PATENT DOCUMENTS

| | | |
|---|---|---|
| EP | 0 432 560 A2 | 11/1990 |
| EP | 0 630 629 A1 | 12/1994 |
| EP | 0 668 058 A1 | 8/1995 |
| EP | 0 808 606 A1 | 11/1997 |
| EP | 0 908 139 A1 | 4/1999 |
| EP | 0 919 193 A1 | 6/1999 |
| EP | 0 920 835 A1 | 6/1999 |
| EP | 0993806 A2 | 4/2000 |
| EP | 0993806 A3 | 6/2000 |
| GB | 2 140 695 A | 12/1984 |
| GB | 2 214 428 A | 9/1989 |
| GB | 2 233 561 | 1/1991 |
| GB | 2 214 428 B | 6/1991 |
| GB | 2267827 | 12/1993 |
| WO | WO 87/04081 | 7/1987 |
| WO | WO 88/00481 | 1/1988 |
| WO | WO 94/03142 | 2/1994 |
| WO | WO 94/14383 | 7/1994 |
| WO | WO 94/14715 | 7/1994 |
| WO | WO 94/18881 | 9/1994 |
| WO | WO 95/01757 | 1/1995 |
| WO | WO 95/15715 | 6/1995 |
| WO | WO 95/17127 | 6/1995 |
| WO | WO 96/00033 | 1/1996 |
| WO | WO 97/10753 | 3/1997 |
| WO | WO 97/40751 | 11/1997 |
| WO | WO 98/10705 | 3/1998 |
| WO | WO 98/17182 | 4/1998 |
| WO | WO 98/27869 | 7/1998 |
| WO | WO 98/48703 | 11/1998 |
| WO | WO 98/49947 | 11/1998 |
| WO | WO 99/08585 | 2/1999 |
| WO | WO 99/09892 | 3/1999 |
| WO | WO 99/16367 | 4/1999 |
| WO | WO 00/06041 | 2/2000 |
| WO | WO 00/10466 | 3/2000 |
| WO | WO 00/15119 | 3/2000 |
| WO | WO 03/001969 | 1/2003 |
| WO | WO 03/001998 | 1/2003 |

OTHER PUBLICATIONS

New Helper Instrument in Cardiac Surgery—D. Roux, M.D.; G. Fournial, M.D.; Y. Glock, M.D.; P. Dalous, M.D.; and P. Puel, M.D., Annal Thorac Surg. 1989;48:595-6.

Coronary Artery Bypass Without Cardiopulmonary Bypass, Pfister et al, The Annals of Thoracic Surgery, vol. 54 #6 Dec. 1992 pp. 1085-1092.

Coronary Artery Operation Supported by the Hemopump: An Experimental Study on Pig, U Lonn, MD; B Peterzen, MD; H Granfeldt, MD; and H Casimir-Ahn, MD, Ph.D. The Annals of Thoracic Surgery, vol. 58, No. 1, Jul. 1994, pp. 516-523.

Regional Cardiac Wall Immobilization for Open Chest and Closed Chest Coronary Artery Bypass Grafting on the Beating Heart: The 'Octopus' Method, Circulation, vol. 92. No. 8 Supplement 1, I-177 (Oct. 15, 1995).

A Minimally Invasive Surgical Method for Coronary Revascularization—Preliminary Experience in Five Patients, MC Robinson, DR Gross, and W Zeman, Circulation, (Oct. 15, 1995) vol. 92, No. 8, I-176.

Coronary Artery Bypass Grafting Without Cardiopulmonary Bypass and Without Interruption of Native Coronary Flow Using a Novel Astamosis Site Restraining Device ("Octopus"), C. Borst et al., Journal of the American College of Cardiology, vol. 27, No. 6, 1356-1364 (May 1996).

Cardiogenic Shock Complicating Acute Myocardial Infarction: the Use of Coronary Angioplasty and the Integration of the New Support Device into Patient Management, GM Gacioch, MD; Stephen G. Ellism, MD, FACC; L Lee, MD; ER Bates, MD, FACC; M Kirsh, MD, FACC; JA Walton, MD, FACC; EH Topol, MD, FACC, Journal of the American College of Cardiology, vol. 19, No. 3, Mar. 1, 1992.

Reoperative Coronary Artery Bypass Grafting Without Cardiopulmonary Bypass, WJ Fanning, MD; GS Kakos, MD; and TE Williams, Jr., MD, Ph.D., The Annals of Thoracic Surgery, vol. 55, No. 2, Feb. 1993, pp. 486-489.

Enhanced Preservation of Acutely Ischemic Myocardium with Transeptal Left Ventricular Assist, JD Fonger, MD; Y Zhou, MD; H Matsuura, MD; GS Aldea, MD; and RJ Shemin, MD, The Annals of Thoracic Surgery, vol. 57, No. 3, Mar. 1994, pp. 570-575.

Transcatheter Radiofrequency Ablation of Atrial Tissue Using a Suction Catheter, Th Lavergne et al. (PACE, vol. 12, Jan. 1989, Part II, pp. 177-186.

Placement of Coronary Artery Bypass Graft without Pump Oxygenator, Trapp et al., Journal of The Society of Thoracic Surgeons and The Southern Thoracic Surgical Assn. vol. 19. No. 7 Jan. 1975.

Experimental Videothoracoscopic Cannulation of the Left Atrial Appendix: A Feasible Rapid Approach For Initiating Left Heart Bypass? PF Gründeman; DW Meijer; JJG Bannenberg; R tukkie; and PJ Klopper, Surgical Endoscopy (1993) 7: 511-513.

The Last Operation: Techniques and Results Before and After the Stabilization Era, Antonio M. Calafiore, MD; Giuseppe Vitolla, MD; Valerio Massei, MD; Giovanni Teodori, MD; Gabriele Di Giammarco, MD; Teresa Iovino, MD and Angela Iaco, MD; Ann Thorac Surg 1998; 66:998-1001.

Hybrid-Type Stabilizer for Off-Pump Direct Coronary Artery Bypass Grafting, by: Toshio Konishi, M.D.; Kazuhiko Higuchi, M.D.;

Mutumu Fukata, M.D.; Shinji Akisima, M.D.; and Shiji Fukuda, M.D.; Ann Thorac Surgery 1998; 66:961-2.

A.J. Delrossi, M.D., and G.M. Lemore, M.D., A New Retractor to Aid in Coronary Artery Surgery, The Annals of Thoracic and Cardiovascular Surgery, vol. 36 Jul. 1983, pp. 101-102.

Stephen Westaby, FRCS and Federico J. Benetti, M.D.; Less Invasive Coronary Surgery: Consensus from the Oxford Meeting, Annals of Thoracic Surgery 1996, 62:924-31.

Kolessov V.I. The Surgery of Coronary Arteries of the Heart, Leningrad, Meditsina, 1977, pp. 360. (Russian Article).

Mammary Artery-Coronary Artery Anastomosis as Method of Treatment for Angina Pectoris, V.I Kolessov, MD/Thoracic and Cardiovascular Surgery, vol. 54, No. 4, Oct. 1967 pp. 535-544.

Direct Myocardial Revascularization by Saphenous Vein Graft, R.G. Favaloro, MD; DG Effler, MD; LK Groves, MD; WG Sheldon, MD; and FM Sones, Jr., MD / The Annals of Thoracic Surgery, vol. 10, No. 2, Aug. 1970.

A Simple Technique and Device To Provide a Bloodless Operative Field in Coronary Artery Surgery Without Cross-Clamping the Aorta, M. Riahi, RJ Schlosser and LA Tomastis/The Journal of Thoracic and Cardiovascular Surgery, vol. 66, No. 6, Dec. 1973, pp. 974-978.

To Use or Not To Use the Pump Oxygenator in Coronary Bypass Operations, Drs. WG Trapp and R. Bisarya/The Annals of Thoracic Surgery, vol. 19, No. 1, Jan. 1975, pp. 108-109.

A Prospective Evaluation of the Pulsatile Assist Device, GL Zumbro, Jr., MD; G Shearer, CCP; ME Fishback, MD; and RF Galloway, MD / The Annals of Thoracic Surgery, vol. 28, No. 2 Aug. 1979, pp. 269-273.

Preservation of Interventricular Septal Function in Patients Having Coronary Artery Bypass Grafts Without Cardiopulmonary Bypass, CW Akins, MD; CA Boucher, MD; and GM Pohost, MD / American Heart Journal, vol. 107, No. 2, Feb. 1984, pp. 304-309.

Coronary Artery Revascularization Without Cardiopulmonary Bypass, R. Archer, DO; DA Ott, MD; R. Parravicini, MD; DA Cooley, MD; GJ Reul, MD; OH Frazier, MD; JM Duncan, MD; JJ Livesay, MD and WE Walker, MD, Texas Heart Institute Journal, vol. 11, No. 1, Mar. 1984, pp. 52-57.

Direct Myocardial Revascularization Without Cardiopulmonary Bypass, E. Buffolo; JCS Andrade, J Succi; LEV Leao; and C Gallucci. Thoac. Cardiovasc. Surgeon, 33 (1985) pp. 26-29.

Direct Coronary Surgery with Saphenous Vein Bypass Without Eigher Cardiopulmonary Bypass or Cardiac Arrest, FJ Benetti, The Journal of Cardiovascular Surgery, vol. 26, No. 3, May-Jun. 1985, pp. 217-222.

Heart-Mechanical Assist Device Interaction, JY Kresh; PLM Kerkhof; SM Goldman; and SK Brockman, Trans. Am. Soc. Artif. Intern. Organs, vol. XXXII, 1986, pp. 437-443.

Delayed Recovery of Severaly 'Stunned' Myocardium with the Support of a Left Ventricular Assist Device after Coronary Artery Bypass Graft Surgery, CM Ballantyne MD; MS verani, MD, FACC; HD Short, MD; C Hyatt, BSN, RN; GP Noon, MD, FACC, Journal of the American College of Cardiology, vol. 10, No. 3, Sep. 1987, pp. 710-712.

Long-Term Follow-up of Survivors of Postcardiotomy Circulatory Support, SA Ruzevich; KR Kanter; DG Pennington; MT Swartz; LR McBride; and DT Termuhlen, Trans. Am. Soc. Artif. Intern. Organs, vol. XXXIV, 1988, pp. 116-124.

Extended Clinical Support with an Implantable Left Ventricular Assist Device, MG McGee; SM Parnis; T Nakatani; T Myers; K Dasse; WD Hare; JM Duncan; VL Poirier; and OH Frazier, Trans Am. Soc. Artif. Intern. Organs, vol. XXXV, 1989, pp. 614-616.

Current Status of Cardiac Surgery: A 40-Year Review, WE Richenbacher, MD; JL Myers, MD, FACC; JA Walhausen, MD, FACC, Journal of American College of Cardiology, vol. 14, No. 3, Sep. 1989, pp. 535-544.

Transfemoral Placement of the Left Ventricular Assist Device "Hemopump" During Mechanical Resuscitation, KH Scholz; U Tebbe; M Chemnitius; H Kreuzer; T Schroder; JP Hering; P Uhlig; G Hellige; HJ Grone; R Autschbach; B Schorn; W Ruschewski; and H Dalichau, Thoracic and Cardiovascular Surgeon, vol. 38 (1990) pp. 69-72.

Direct Mechanical Ventricular Actuation for Cardiac Arrest in Humans, MP Anstadt, MD; RL Bartlett, MD; JP Malone, MD, FCCP; and GL Anstadt, VMD; Chest, vol. 100, No. 1, Jul. 1991.

Direct Myocardial Revascularization Without Extracorpoeal Circulation, FJ Benetti, MD; G Naselli, MD; M Wood, MD; and L Geffner, MD, Chest, vol. 100. No. 2, Aug. 1991, pp. 312-316.

Current status of claims in U.S. Appl. No. 10/643,299, filed Aug. 19, 2003 (10 pages).

Specifications and drawings in U.S. Appl. No. 10/643,299, filed Aug. 19, 2003 (72 pages).

U.S. Appl. No. 10/643,299, Notice of Allowance mailed Oct. 10, 2007.

U.S. Appl. No. 10/643,299, Response mailed Jan. 8, 2007.

U.S. Appl. No. 10/643,299, Office Action mailed Sep. 7, 2006.

* cited by examiner

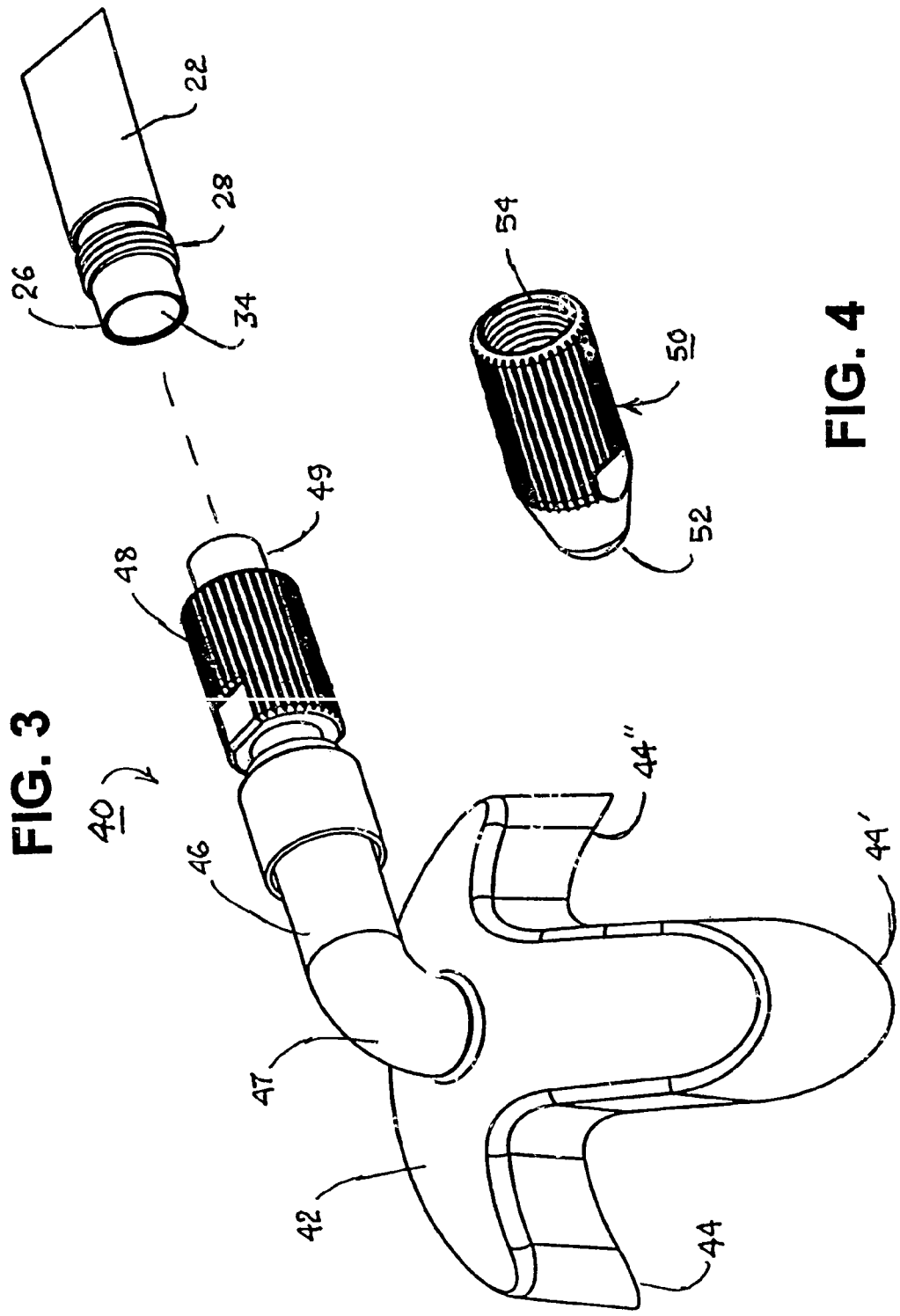

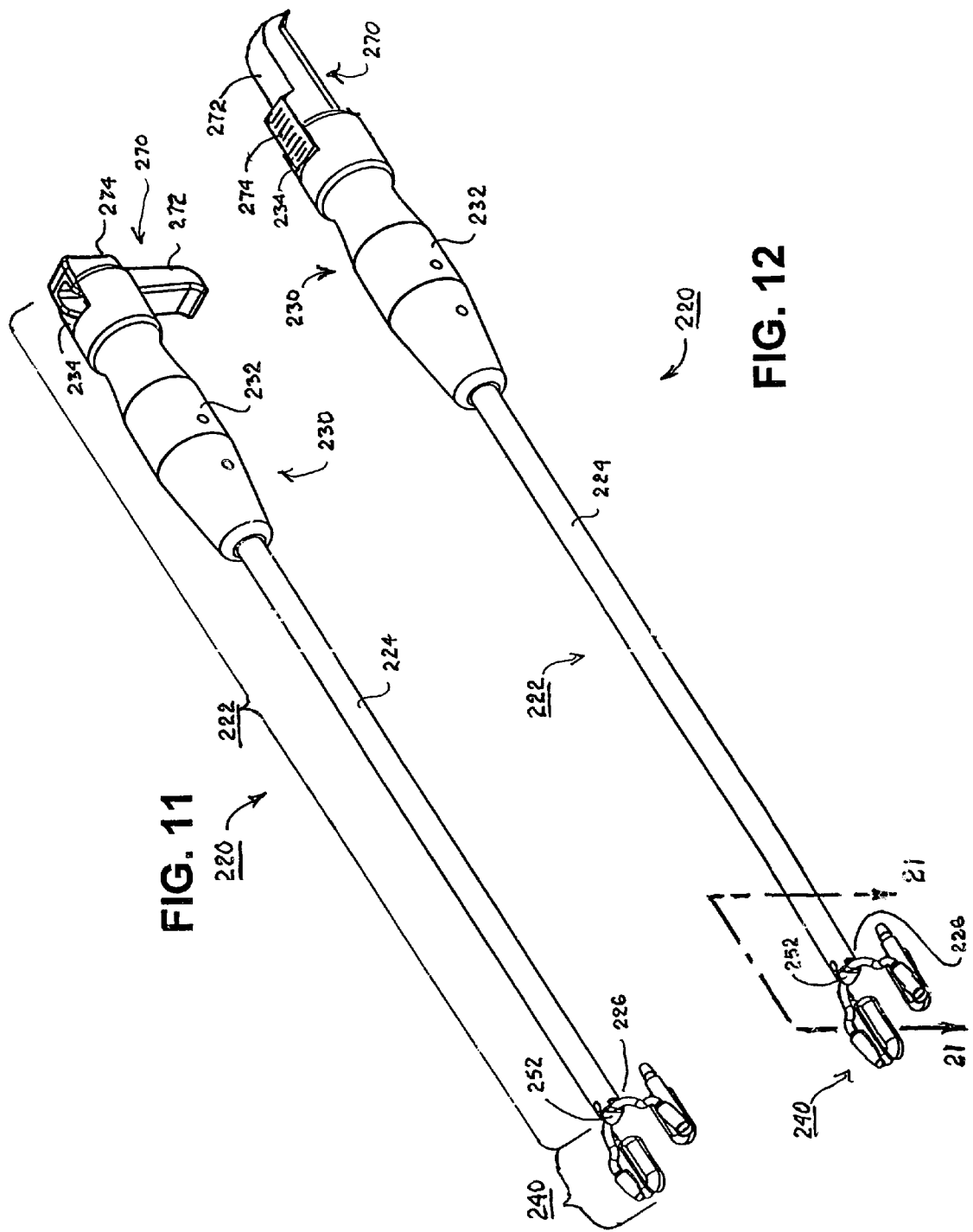

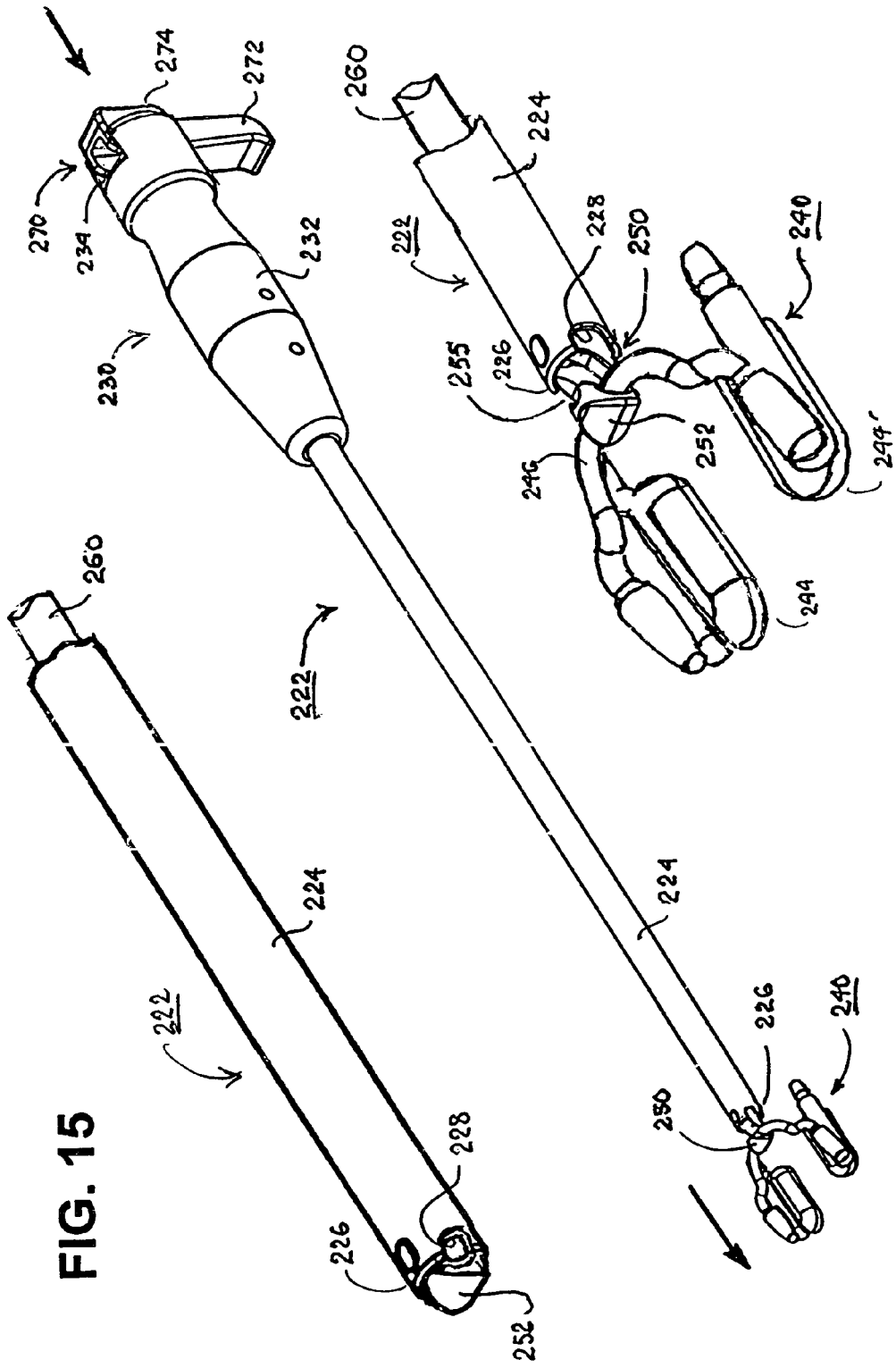

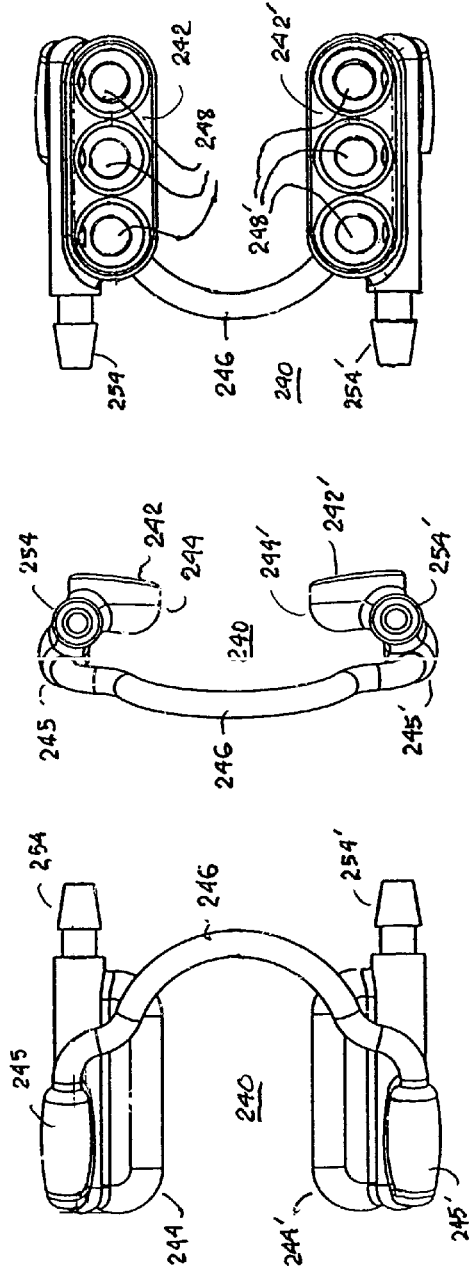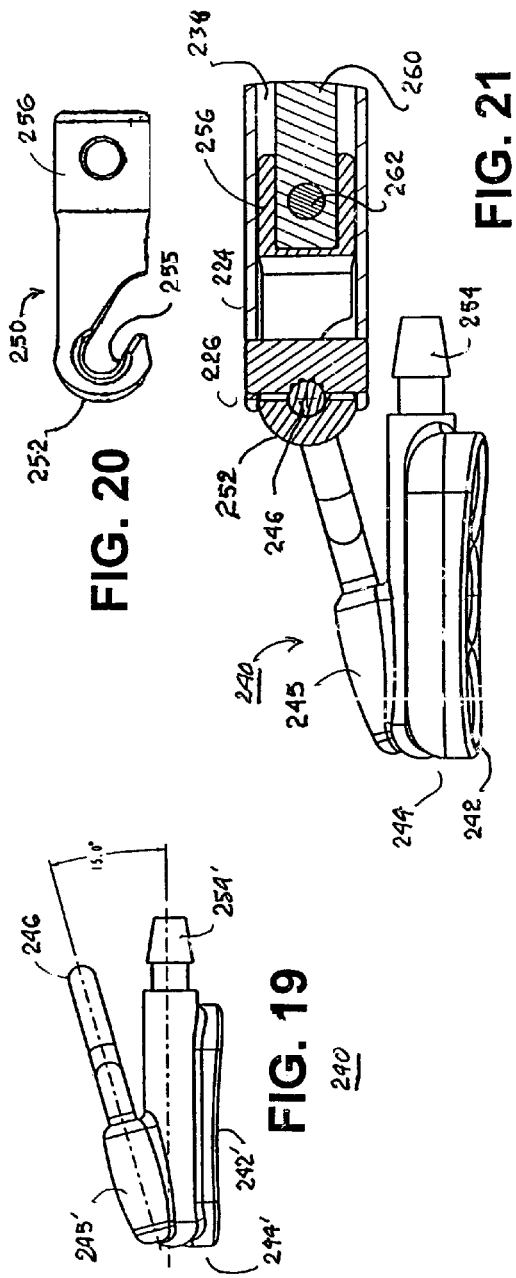

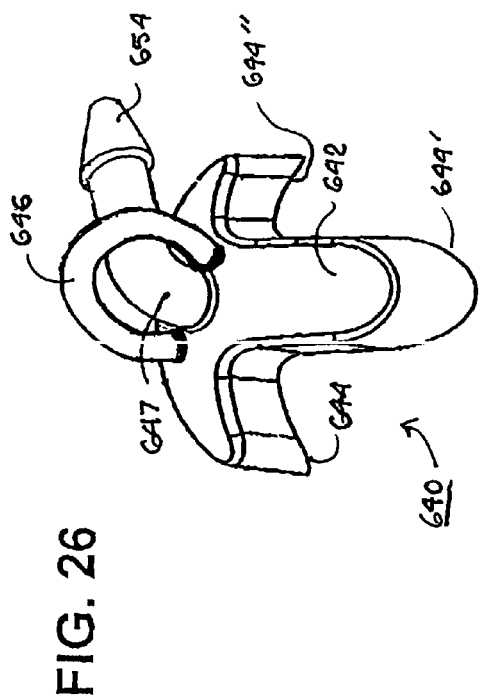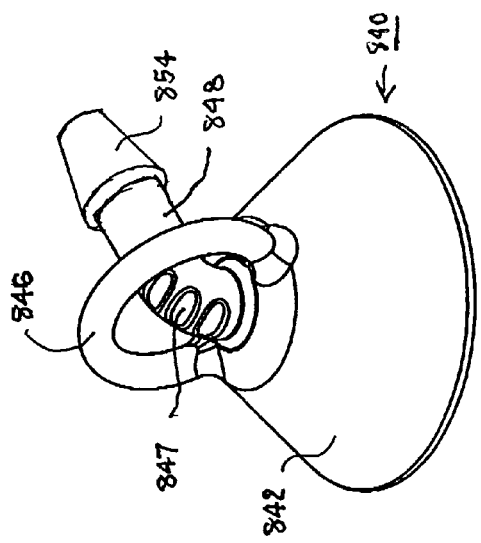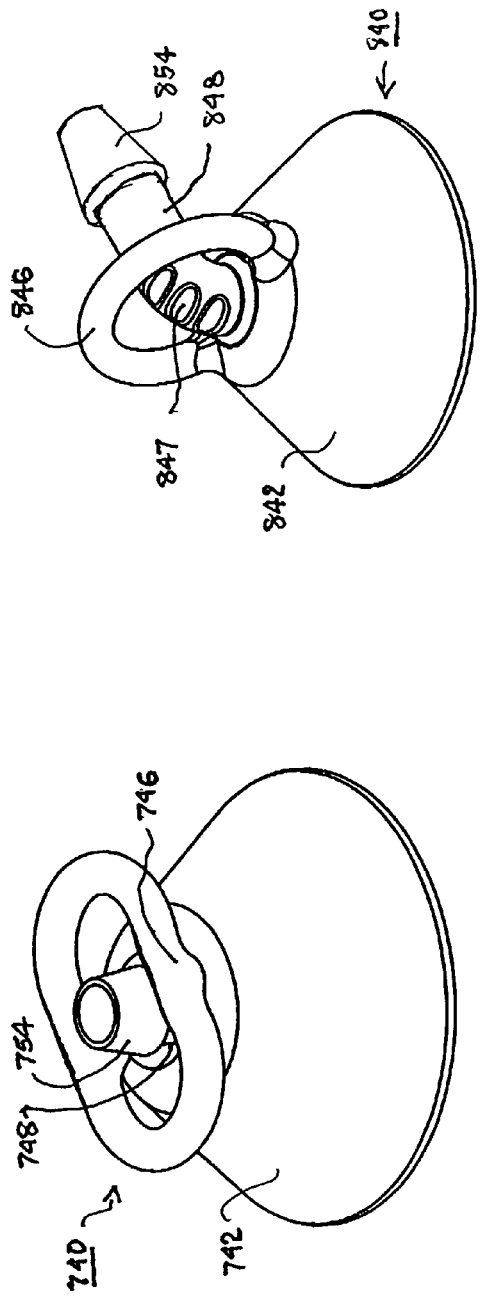

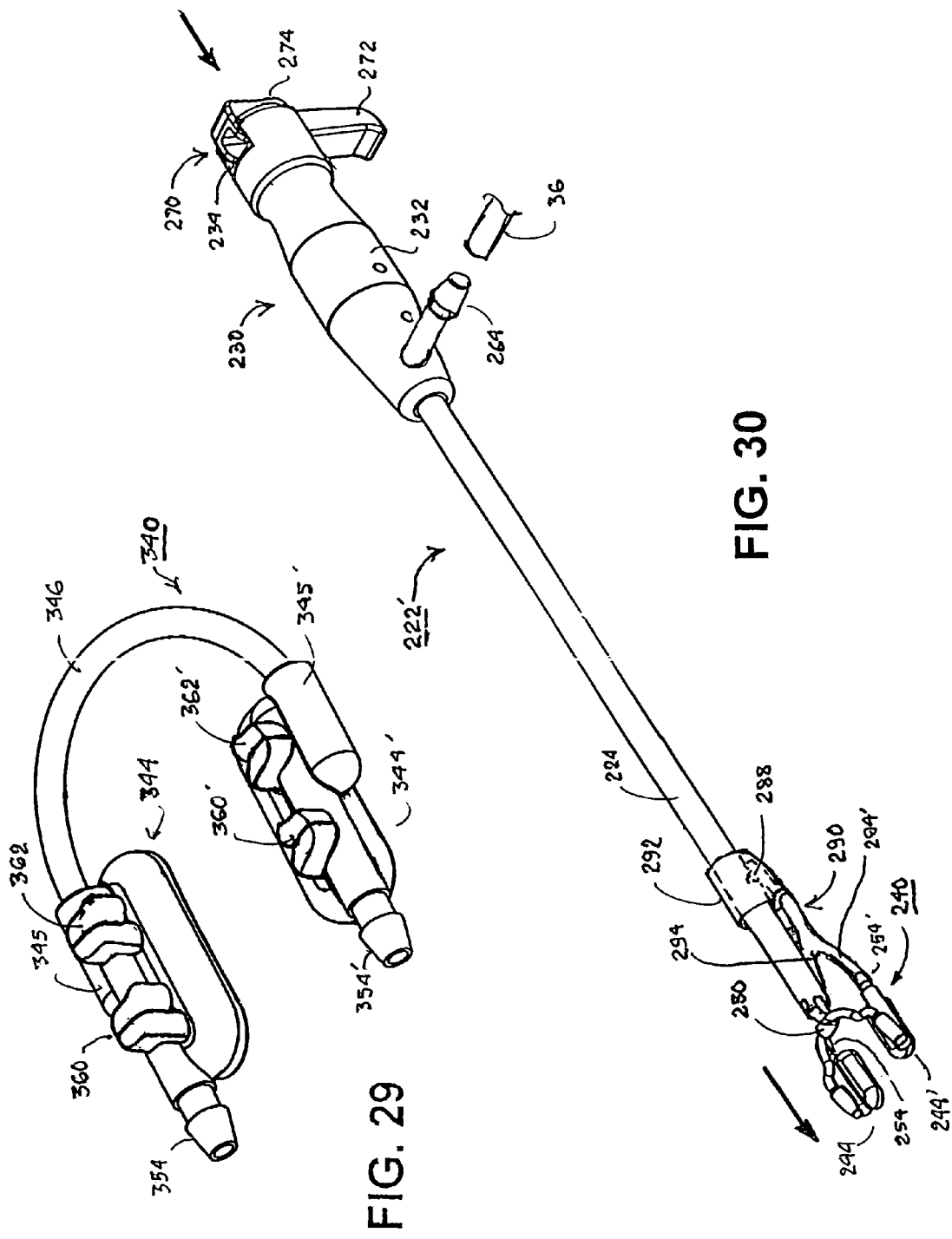

METHODS AND APPARATUS PROVIDING SUCTION-ASSISTED TISSUE ENGAGEMENT THROUGH A MINIMALLY INVASIVE INCISION

RELATED APPLICATIONS

This application is a continuation-in-part of U.S. patent application Ser. No. 10/643,299 filed Aug. 19, 2003 now U.S. Pat. No. 7,338,434, entitled METHOD AND SYSTEM FOR ORGAN POSITIONING AND STABILIZATION in the names of Philip J. Haarstad et al.

This application claims benefit of Provisional No. 60/404,969 filed Aug. 21, 2002, and Provisional No. 60/424,243 filed Nov. 6, 2002.

FIELD OF THE INVENTION

This invention relates generally to suction-assisted tissue-engaging devices, systems and methods that can be employed through minimal surgical incisions to engage, i.e., position, manipulate, stabilize, and/or hold tissue, e.g., tissue of a body organ, during a medical procedure through a suction member or head applied to the tissue, particularly to apply suction to the heart to engage and position, manipulate, stabilize, and/or hold the beating heart during cardiac surgery.

BACKGROUND OF THE INVENTION

Coronary artery disease remains the leading cause of morbidity and mortality in Western societies. Coronary artery disease is manifested in a number of ways. For example, disease of the coronary arteries can lead to insufficient blood flow to various areas of the heart. This can lead to the discomfort of angina and the risk of ischemia. In severe cases, acute blockage of coronary blood flow can result in irreversible damage to the myocardial tissue including myocardial infarction and the risk of death.

A number of approaches have been developed for treating coronary artery disease. In less severe cases, it is often sufficient to merely treat the symptoms, with pharmaceuticals, or treat the underlying causes of the disease, with lifestyle modification. In more severe cases, the coronary blockage can be treated endovascularly or percutaneously using techniques such as balloon angioplasty, atherectomy, laser ablation, stents, and the like.

In cases where these approaches have failed or are likely to fail, it is often necessary to perform a coronary artery bypass graft (CABG) procedure. CABG surgery, also known as "heart bypass" surgery, generally entails the use of a graft or conduit to bypass the coronary obstruction and, thereby provide blood flow to the downstream ischemic heart tissues. The major objective of any CABG procedure is to perform a technically perfect anastomosis of the graft with the vessel. Creation of a technically perfect anastomosis is generally complex, tedious, time consuming and its success is highly dependent on a surgeon's skill level.

The CABG procedure is typically conducted on an arrested heart while the patient is on a cardiopulmonary bypass (CPB) circuit, also known as a "heart-lung machine" that provides continuous systemic blood circulation, while cardioplegic cardiac arrest enables meticulous anastomosis suturing in a bloodless, still-heart, operating field. In a CPB procedure performed as an adjunct to a CABG procedure, the patient's venous blood that normally returns to the right atrium is diverted to a CPB system or circuit that supplies oxygen to the blood and removes carbon dioxide from the blood and returns the blood, at sufficient pressure, into the patient's aorta for further distribution through the arterial system to the body. Creation of the CPB circuit typically entails arterial and venous cannulation, connecting the bloodstream to a heart-lung machine, cooling the body to about 32° Celsius, cross clamping of the aorta, and cardioplegic perfusion of the coronary arteries to arrest and cool the heart to about 4° Celsius. The arrest or stoppage of the heart is generally required because the constant pumping motion of the beating heart would make surgery upon the heart difficult in some locations and extremely difficult if not impossible in other locations. Generally, such a CPB system requires several separate components, including an oxygenator, several pumps, a reservoir, a blood temperature control system, filters, and flow, pressure and temperature sensors.

A blood vessel or vessels for use in the graft procedure are harvested or mobilized from the patient. In the majority of patients, obstructed coronary arteries are bypassed using an in situ internal mammary artery (IMA) or a reversed segment of saphenous vein harvested from a leg although other graft vessels may also be used. For this reason, CABG surgery is typically performed through a median sternotomy, which provides access to the heart and to all major coronary branches. A median sternotomy incision begins just below the sternal notch and extends slightly below the xiphoid process. A sternal retractor is used to spread the left and right rib cage apart for optimal exposure of the heart. Hemostasis of the sternal edges is typically obtained using electrocautery with a ball-tip electrode and a thin layer of bone wax. The pericardial sac is opened thereby achieving direct access to the heart. One or more grafts are attached to the relevant portion of a coronary artery (or arteries) to bridge the obstruction while the heart is in cardiac arrest. Then, the patient is weaned from CPB, the heart is restarted, and cannulation is discontinued. The surgical incisions in the chest are then closed.

The CABG procedure is generally expensive, lengthy, traumatic and subject to patient risk. The arrest of the heart and the use of the CPB circuit add to the time and expense of the CABG procedure and present a number of risk factors to the patient. The initiation of global (hypothermic) cardiac arrest may result in global myocardial ischemia, and cross clamping the ascending aorta may contribute to the patient experiencing a post-operative stroke. In fact, recent studies have shown aortic clamping and manipulation may release atherosclerotic debris into the bloodstream, resulting in neurological injury. Exposure of blood to foreign surfaces results in the activation of virtually all the humoral and cellular components of the inflammatory response, as well as some of the slower reacting specific immune responses. A systemic inflammatory response can result due to the interactions of blood elements with the artificial material surfaces of the components of the CPB circuit. Other complications associated with cardiopulmonary bypass include loss of red blood cells and platelets due to shear stress damage. In addition, cardiopulmonary bypass requires the use of an anticoagulant, such as heparin that increases the risk of hemorrhage. Cardiopulmonary bypass also sometimes necessitates giving additional blood to the patient that may expose the patient to blood-borne diseases, if it is from a source other than the patient.

Therefore, a number of cardiac surgical procedures have been developed or proposed to enable off-pump, beating heart, CABG procedures either through a median sternotomy or employing minimally invasive procedures and even totally endoscopic procedures with access through ports extending through the chest wall into the thoracic cavity. For example, Trapp and Bisarya, in "Placement of Coronary Artery Bypass Graft Without Pump Oxygenator", *Annals Thorac. Surg.*, Vol. 19, No. 1, (January 1975), pp. 1-9, immobilized the area of the bypass graft by encircling sutures deep enough to incorp enough muscle to suspend an area of the heart and prevent damage to the coronary artery. More recently, Fanning et al. also reported, in "Reoperative Coronary Artery Bypass Grafting Without Cardiopulmonary Bypass", *Annals Thorac. Surg.*, Vol. 55, (February 1993), pp. 486-489, immobilizing the area of the bypass graft with stabilization sutures.

Other approaches of stabilizing at least a portion of the heart to facilitate CABG or other procedures involve applying pressure against the heart wall as exemplified by the stabilization apparatus disclosed in U.S. Pat. Nos. 5,875,782, 6,120, 436, and 6,331,158, for example. In one embodiment disclosed in the '436 patent, a U-shaped platform is pressed against the heart surface exposed through a thoracotomy and maintained there by suturing the platform to the myocardium or by attaching the platform to the end of an adjustable arm. The adjustable arm is mounted to a rib retractor maintaining the ribs spread apart, and the adjustable arm can be adjusted to direct pressure through the platform against the heart to stabilize it.

In addition, mechanical systems for lifting the heart, particularly to enable access to the heart for performing valve surgery, have been proposed as exemplified in the apparatus disclosed in U.S. Pat. No. 6,558,318.

In one embodiment disclosed therein, a tissue positioning tool is provided comprising a tool support member adapted to be mounted to the patient's body, an elongated shaft supported by the tool support member adapted to be passed through a small incision, and a tissue supporting member having a surface adapted to contact tissue, e.g., the heart, that can be attached and detached from the elongated shaft. In use, the tissue support member is introduced into the thoracic cavity through a first percutaneous penetration, and the elongated shaft is introduced through a second percutaneous penetration. The tissue-supporting member is connected to the shaft within the thoracic cavity to form a tissue-positioning tool. Assembling the tool within the thoracic cavity allows the use of tissue-engaging devices having parts and surfaces too large to be introduced through the typically smaller penetration from which the shaft of the tool extends.

These mechanical systems for applying force against or lifting the heart are less efficacious than systems that apply suction against the heart to engage the heart. Suction-assisted tissue-engaging devices, such as the various models of the Medtronic® Octopus 3™ tissue stabilizer and or Starfish™ heart positioner and accessories available from the assignee of the present invention, use suction for stabilizing or positioning, respectively, tissue of an organ. The Medtronic® Octopus 3™ tissue stabilizer is approved for use in applying suction to a surface of the heart to stabilize the heart tissue at the site of engagement while the heart is beating to facilitate a surgical procedure, e.g., to perform an anastomosis in the course of a CABG procedure. The Starfish™ heart positioner is approved for use in applying suction to a surface of the heart, particularly near the apex of the heart, to move and reposition the heart to achieve better access to areas that would otherwise be difficult to access, such as the posterior or backside of the heart. For example, the surgeon can bring an anastomosis site into better view by supporting and rotating the heart using the Starfish™ heart positioner. The surgeon can also use the Octopus 3™ tissue stabilizer in the same procedure to stabilize the anastomosis site. See, for example, commonly assigned U.S. Pat. Nos. 5,836,311, 5,927,284, 6,015,378, 6,464,629, and 6,471,644 and U.S. patent application Ser. No. 09/678,203, filed Oct. 2, 2000, and European Patent Publication No. EP 0 993 806describing aspects of the Octopus 3™ heart stabilization system and commonly assigned U.S. Pat. No. 6,676,597disclosing aspects of the Starfish™ heart positioner.

The Octopus 3™ tissue stabilizer employs a pair of elongated, malleable suction pads mounted to extend in a U-shape from the distal end of a malleable, articulating arm, and a tissue spreading mechanism that the surgeon can employ to spread the elongated arms apart. As described in the above-referenced '629 patent, after the suction pods are applied to the heart surface, tightening a cable extending through the arm fixes the arm in place. Then, the suction pods may be spread apart from each other to tighten the surface of the cardiac tissue lying between the suction pods. In one embodiment, fixation of the articulating arm as well as the spreading apart of the suction pods may occur concurrently or almost concurrently through the tensioning of a single cable.

The Starfish™ heart positioning system employs a three appendage, silicone head mounted to the distal end of a malleable, articulating arm. The silicone head is shaped so that the flexible appendages or legs diverge apart and can engage the heart surface particularly adjacent to the apex of the heart to lift and position the heart when suction is applied.

Further suction-assisted tissue-engaging devices for use in cardiac surgery through a sternotomy are disclosed in U.S. Pat. No. 5,799,661 in PCT Publication WO 01/17437 A2 wherein a conical or helmet shaped suction member is mounted to the distal end of an articulating arm and is adapted to apply suction to the apex of the heart and lift the heart. Other suction-assisted tissue-engaging devices for cardiac surgery having circular or horseshoe-shaped suction members introduced through a sternotomy are disclosed in U.S. Pat. Nos. 5,868,770, 5,782,746, and 6,071,295.

These suction-assisted, tissue-engaging devices are used in open chest sternotomy procedures that involve making a 20 to 25 cm incision in the chest of the patient, severing the sternum, cutting and peeling back various layers of tissue in order to give access to the heart and arterial sources, and fitting a retractor across the incision to maintain the ribs spread apart. The articulating arms of the above-described Medtronic® Octopus 3™ tissue stabilizer and or Starfish™ heart positioner are mounted to the Medtronic® OctoBase™ retractor.

Such median sternotomies are highly traumatic and typically require many sutures or staples to close the incision and 5 to 10 wire hooks to keep the severed sternum together during recovery. Such surgery often carries additional complications such as instability of the sternum, post-operative bleeding, and mediastinal infection. The thoracic muscle and ribs are also severely traumatized, and the healing process results in an unattractive scar. Post-operatively, most patients endure significant pain and must forego work or strenuous activity for a long recovery period.

Many minimally invasive surgical techniques and devices have been proposed or introduced in order to reduce the risk of morbidity, expense, trauma, patient mortality, infection, and other complications associated with open-chest cardiac surgery. Less traumatic limited open chest techniques using an abdominal (sub-xyphoid) approach or, alternatively, a "Chamberlain" incision (an approximately 8 cm incision at the sternocostal junction), have been developed to lessen the operating area and the associated complications. In recent years, a growing number of surgeons have begun performing coronary artery bypass graft (CABG) procedures using minimally invasive direct coronary artery bypass grafting (MID-CAB) surgical techniques and devices. Using the MIDCAB method, the heart typically is accessed through a mini-thoracotomy (i.e., a 6 to 8 cm incision in the patient's chest) that avoids the sternal splitting incision of conventional cardiac surgery. A MIDCAB technique for performing a CABG procedure is described in U.S. Pat. No. 5,875,782, for example.

Other minimally invasive, percutaneous, coronary surgical procedures have been proposed or introduced that employ multiple small trans-thoracic incisions to and through the pericardium, instruments advanced through the incisions, and a thoracoscope to view the accessed cardiac site while the procedure is performed as shown, for example, in U.S. Pat. Nos. 6,332,468, 5,464,447, and 5,716,392. As stated in the '468 patent, instruments advanced through the incisions can include electrosurgical tools, graspers, forceps, scalpels, electrocauteries, clip appliers, scissors, etc. Each incision is maintained open by insertion of a cannula or port through the incision so that the instruments can be advanced through the lumen of the cannula or port. If a trocar is used, a trocar rod is inserted into the trocar sleeve, and the sharpened tip of the trocar rod is advanced to puncture the abdomen or chest to create the incision into the thoracic cavity. The trocar rod is then withdrawn leaving the trocar sleeve in place so that a surgical instrument can be inserted into the thoracic cavity through the trocar sleeve lumen.

In such procedures, the surgeon can stop the heart by utilizing a series of internal catheters to stop blood flow through the aorta and to administer cardioplegia solution. The endoscopic approach typically also utilizes groin cannulation to establish CPB and an intra-aortic balloon catheter that functions as an internal aortic clamp by means of an expandable balloon at its distal end used to occlude blood flow in the ascending aorta. A full description of an example of one preferred endoscopic technique is found in U.S. Pat. No. 5,452,733, for example.

The above-described Medtronic® Octopus 3™ tissue stabilizer and or Starfish™ heart positioner are not sized and designed to fit through such a minimally invasive incision or the lumen of a cannula or port or trocar sleeve. The use of the an early version of an Octopus™ tissue stabilizer through a minimally invasive incision without CPB to stabilize a site of the beating heart is disclosed in one embodiment in commonly assigned U.S. Pat. Nos. 6,464,630 and 6,394,948, for example. In this embodiment, the tissue stabilizer employs a single elongated suction pod fixed at the distal end of an elongated shaft to extend substantially axially and to the elongated shaft. It is necessary to employ two such elongated shafts and suction pods to place the suction pads on either side of the heart surface to be stabilized. Consequently, it would be difficult to position two such elongated shafts and suction pads through a single minimally invasive incision of parallel incisions. Thus, the suggested approach offers little advantage over employing a single large incision or sternotomy.

A modification of the Octopus™ tissue stabilizer is suggested in the above-referenced commonly assigned pending application Ser. No. 09/678,203, wherein the two suction pods are supported fixed to the distal end of the tissue stabilizer in a manner that enables the suction pods to be collapsed into a small diameter to facilitate insertion through the lumen of a cannula or port or trocar sleeve.

Other methods and apparatus that are introduced through percutaneously placed ports or directly through small transthoracic incisions for accessing the pericardial space employ suction devices to grip the pericardium or epicardium as disclosed, for example, in U.S. Pat. Nos. 4,991,578, 5,336,252, 5,827,216, 5,868,770, 5,972,013, 6,080,175, and 6,231,518. The suction devices are typically configured like a catheter or tube having a single suction lumen and typically having a further instrument delivery lumen. The suction lumen terminates in a single suction lumen end opening through the device distal end in the '578, '252, '175, '770, and '013 patents and through the device sidewall in the '216 and '518 patents. Certain of these patents recite that the applied suction draws a "bleb," i.e., a locally expanded region of the pericardium, into the suction lumen or a suction chamber at the device distal end. A needle can then be advanced into the bleb and used to draw off fluids or deliver drugs into the pericardial space, or the like. In addition, it is suggested in these patents that treatment devices including catheters, guidewires, and electrodes, e.g., defibrillation electrodes, can be advanced into the pericardial space through a device introduction lumen for a variety of reasons. Although theoretically plausible, the ability to reliably maintain a vacuum seal against the pericardium when such treatment devices are advanced can be problematic.

Surgeons have found that the Octopus 3™ stabilization system and Starfish™ heart positioner provide significant benefits in the above-described operative procedures involving relatively large sternotomies or thoracotomies. It would be desirable to be able to enjoy the advantages of such suction-assisted tissue-manipulation systems using minimally invasive procedures for performing coronary procedures or to access and perform a procedure on other body tissue.

SUMMARY OF THE INVENTION

In accordance with the present invention, suction-assisted tissue-engaging devices, systems, and methods are provided that can be employed through minimal surgical incisions to engage body tissue, e.g., tissue of an organ, during a medical procedure through application of suction to the tissue through a suction member of a suction-assisted tissue-engaging device applied to the body tissue.

The suction-assisted tissue-engaging device of the present invention has a first portion and a second portion that can be attached together and detached from one another. The first portion of the suction-assisted tissue-engaging device is introduced into a body cavity through a first incision. The second portion of the suction-assisted tissue-engaging device is then attached to the first portion of the suction-assisted tissue-engaging device via a second incision. The second portion of the suction-assisted tissue-engaging device is then applied against the body tissue by manipulation of the first portion of the suction-assisted tissue-engaging device, and suction is applied through the second portion of the suction-assisted tissue-engaging device to engage the body tissue. The medical procedure is then performed through the second incision while the body tissue is either positioned or stabilized by the applied suction. When the medical procedure is completed, suction is discontinued, the second portion of the suction-assisted tissue-engaging device is detached from the first portion of the suction-assisted tissue-engaging device and withdrawn from the body cavity through the second incision, and the first portion of the suction-assisted tissue-engaging device is retracted through the first incision.

The suction-assisted tissue-engaging device of the present invention can further comprise a third portion that functions when the second portion is detached from the first portion to minimize damage to tissue as the first portion of the suction-assisted tissue-engaging device is introduced into or moved about the body cavity through the first incision.

In preferred embodiments of the present invention, the first portion of the suction-assisted tissue-engaging device is an elongated shaft having a shaft body extending between a proximal shaft handle and shaft body distal end and a shaft body diameter facilitating introduction through a minimally invasive first incision. The second portion comprises a suction member or head that is configured to engage body tissue and function either as an organ positioner or a tissue stabilizer and that can be attached to or detached from the shaft body distal end.

In preferred embodiments of the invention, a fastener is provided at the shaft body distal end for engagement with the suction head to attach or detach the suction head to or from the shaft body distal end either manually or employing a further tool.

In one preferred embodiment, the fastener can be manipulated through the shaft body from the shaft handle to engage or release the suction head. The shaft fastener extends through the shaft body from a shaft fastener proximal end at the shaft handle to a shaft fastener distal end, and the shaft fastener is adapted to be moved to a disengage position to receive or release the suction head fastener element and to an engage position fixedly attaching the suction head to the shaft body distal end. In this embodiment, the fastener at the shaft body distal end is preferably blunted to function as the third portion of the suction-assisted tissue-engaging device so that the shaft body can be advantageously manipulated within the body cavity without causing undesirable tissue damage.

In a further preferred embodiment, the fastener comprises mating fastener elements of the shaft body distal end and the suction head that are adapted to be manipulated manually or with a tool to attach or detach the suction head to or from the shaft body distal end. A separate blunting element is provided with a fastener element that can be manipulated manually or with a tool to attach or detach the blunting element to or from the shaft body distal end. In this embodiment, the blunting element is attached to the shaft body distal end as a third portion of the suction-assisted tissue-engaging device so that the shaft body can be advantageously manipulated within a patient without causing undesirable tissue damage. The blunting element is then detached from the shaft body distal end to enable attachment of the suction head to the shaft body distal end and may be re-attached to the shaft body distal end after the suction head is detached.

The suction head can be introduced into the body cavity through the second incision and attached to the shaft body distal end. In a preferred method of the present invention, the shaft handle is manipulated to pass the shaft body distal end out of the body cavity through the second incision, the suction head is attached to the shaft body distal end outside the patient's body, and the shaft handle is again manipulated to bring the suction head through the second incision into the body cavity.

In use, the proximal handle of the suction-assisted tissue-engaging device is manipulated to orient suction ports of the suction head against the body tissue so that the tissue site is engaged, whereby the elongated shaft body is oriented at a particular operative vector in 3-D space relative to the patient's body. The system of the present invention preferably comprises a support that can be coupled to the elongated shaft to maintain the operative vector while the medical procedure is conducted through the second incision or until it is necessary to change the operative vector.

In a preferred embodiment, the support comprises an elongated, articulating, support arm having an arm distal end that can be attached to and detached from the elongated shaft and an arm proximal end that can be attached to and detached from a fixed reference point. The fixed reference point preferably comprises the frame of the operating table or a rigid rail attached to the operating table frame. The articulating arm body can be manipulated in shape while in a flexible condition or state and maintains the shape in a rigid condition or state.

In use of the system, the arm distal end is coupled to the elongated shaft, and the arm proximal end is coupled to the reference point while the articulating arm is in the flexible state. The elongated shaft is manipulated to the desired operative vector of the elongated shaft, and the articulating arm is rendered rigid to maintain the desired operative vector of the shaft.

At the conclusion of the medical procedure, suction is discontinued, and the elongated shaft is released from the articulating arm. In the preferred method of the present invention, the shaft handle is manipulated to pass the shaft body distal end and attached suction member out of the body cavity through the second incision, and the suction head is detached from the shaft body distal end outside the patient's body. The shaft handle is again manipulated to bring the elongated shaft body back through the second incision into the body cavity and to retract it from the body cavity through the first incision.

The suction-assisted tissue-engaging devices, systems and methods of the present invention are advantageously employed through minimal surgical incisions into the thoracic cavity to obviate the necessity of performing a sternotomy or large thoracotomy to introduce and position the suction head to apply suction to the heart to position and/or stabilize the beating heart to perform a medical procedure.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIG. 3 is a perspective view of a fastener at the shaft body distal end of the elongated shaft adapted to be attached to the suction head of the suction-assisted, tissue-engaging device of FIG. 1;

FIG. 4 is a perspective view of the blunting element adapted to be attached to the shaft body distal end to facilitate advancement of the elongated shaft from a first incision into a body cavity and through a second incision without damaging tissue;

FIG. 11 is a perspective view of a third embodiment of a suction-assisted, tissue-engaging device adapted to be employed with the articulating arm and a support rail as illustrated in FIGS. 1, 5, and 6 particularly to stabilize a region of the heart to perform a medical procedure through the second incision, wherein the fastener of the elongated shaft entraps the suction head within a fastener hook at the shaft body distal end when a toggle at the shaft body proximal end is in neutral position between a locked position and an advanced position;

FIG. 12 is a perspective view of the suction-assisted, tissue-engaging device of FIG. 11 with the suction head locked to the shaft body distal end by movement of a toggle at the shaft body proximal end into the locked position;

FIG. 13 is a perspective view of the suction-assisted, tissue-engaging device of FIG. 11 with the fastener hook extended distally to receive or release the suction head by distal depression of the toggle from the neutral position to the advanced position;

FIG. 14 is an enlarged partial perspective view of the fastener hook in the distally extended position of FIG. 13;

FIG. 15 is a partial perspective view of the shaft body distal end of the shaft illustrated in FIGS. 11-14 with the suction head removed and the fastener hook retracted into a shaft body lumen to function as a blunting element enabling safe manipulation of the elongated shaft body as shown in FIG. 5 within a patient;

FIG. 16 is a top plan view of the suction head of FIGS. 11-14;

FIG. 17 is an end elevation view of the suction head of FIGS. 11-14;

FIG. 18 is a bottom plan view of the suction head of FIGS. 11-14 illustrating the suction ports of the suction pods;

FIG. 19 is a side elevation view of the suction head of FIGS. 11-14;

FIG. 20 is a side elevation view of the fastener hook illustrated in FIGS. 11-15; and FIG. 21 is a cross-section view taken along lines 21-21 of FIG. 12 illustrating the partial retraction of the fastener hook within the elongated shaft body lumen to lock the suction head to the shaft body distal end;

FIG. 26 is a perspective view of a seventh embodiment of a suction head adapted to be coupled with the elongated shaft of FIGS. 11-15 and adapted to be employed with the articulating arm and a support rail as illustrated in FIGS. 1, 5, and 6 particularly to position the heart to perform a medical procedure through the second incision;

FIG. 27 is a perspective view of an eighth embodiment of a suction head adapted to be coupled with the elongated shaft of FIGS. 11-15 and adapted to be employed with the articulating arm and a support rail as illustrated in FIGS. 1, 5, and 6 particularly to position the heart to perform a medical procedure through the second incision;

FIG. 28 is a perspective view of a ninth embodiment of a suction head adapted to be coupled with the elongated shaft of FIGS. 11-15 and adapted to be employed with the articulating arm and a support rail as illustrated in FIGS. 1, 5, and 6 particularly to position the heart to perform a medical procedure through the second incision;

FIG. 29 is a further perspective view of the fourth embodiment of a suction head illustrated in FIG. 23 depicting suture holders on the suture pods;

FIG. 30 is an exploded view of the components of a further embodiment of the elongated shaft illustrated in FIGS. 11-15 and 21-22.

DETAILED DESCRIPTION OF THE INVENTION

In the following detailed description, references are made to illustrative embodiments of methods and apparatus for carrying out the invention. It is understood that other embodiments can be utilized without departing from the scope of the invention. Preferred methods and apparatus are described for accessing the heart surface in the thoracic cavity and stabilizing or positioning the heart as an example of accessing an anatomic space or cavity containing body tissue to stabilize or position the tissue to perform a medical procedure.

The term "medical procedure" may mean any one or more medical or surgical procedures such as, for example cardiac surgery, performed with or without CPB, heart valve repair, heart valve replacement, MAZE procedures, transmyocardial revascularization (TMR), CABG procedures, anastomosis procedures, non-surgical procedures, endoscopic procedures, non-invasive procedures, invasive procedures, port-access procedures, fluoroscopic procedures, beating heart surgery, vascular surgery, neurosurgery, electrophysiology procedures, diagnostic and therapeutic procedures, ablation procedures, ablation of arrhythmias, endovascular procedures, treatment of one or more organs and/or vessels, treatment of the heart, aneurysm repair, aortic aneurysm repairs, imaging procedures of the heart and great vessels, CAT scan procedures, MRI procedures, cardiograms, pharmacological therapies, drug delivery procedures, delivery of biological agents, gene therapies, cellular therapies, cancer therapies, radiation therapies, genetic, cellular, tissue and/or organ manipulation or transplantation procedures, coronary angioplasty procedures, placement or delivery of coated or uncoated stents, LVAD procedures, lead placement procedures, placement of cardiac reinforcement devices, placement of cardiac assistance devices, atherectomy procedures, atherosclerotic plaque manipulation and/or removal procedures, emergency procedures, cosmetic procedures, reconstructive surgical procedures, biopsy procedures, autopsy procedures, surgical training procedures, birthing procedures, congenital repair procedures, and medical procedures that require positioning one or more organs and/or tissues.

Figure 5:
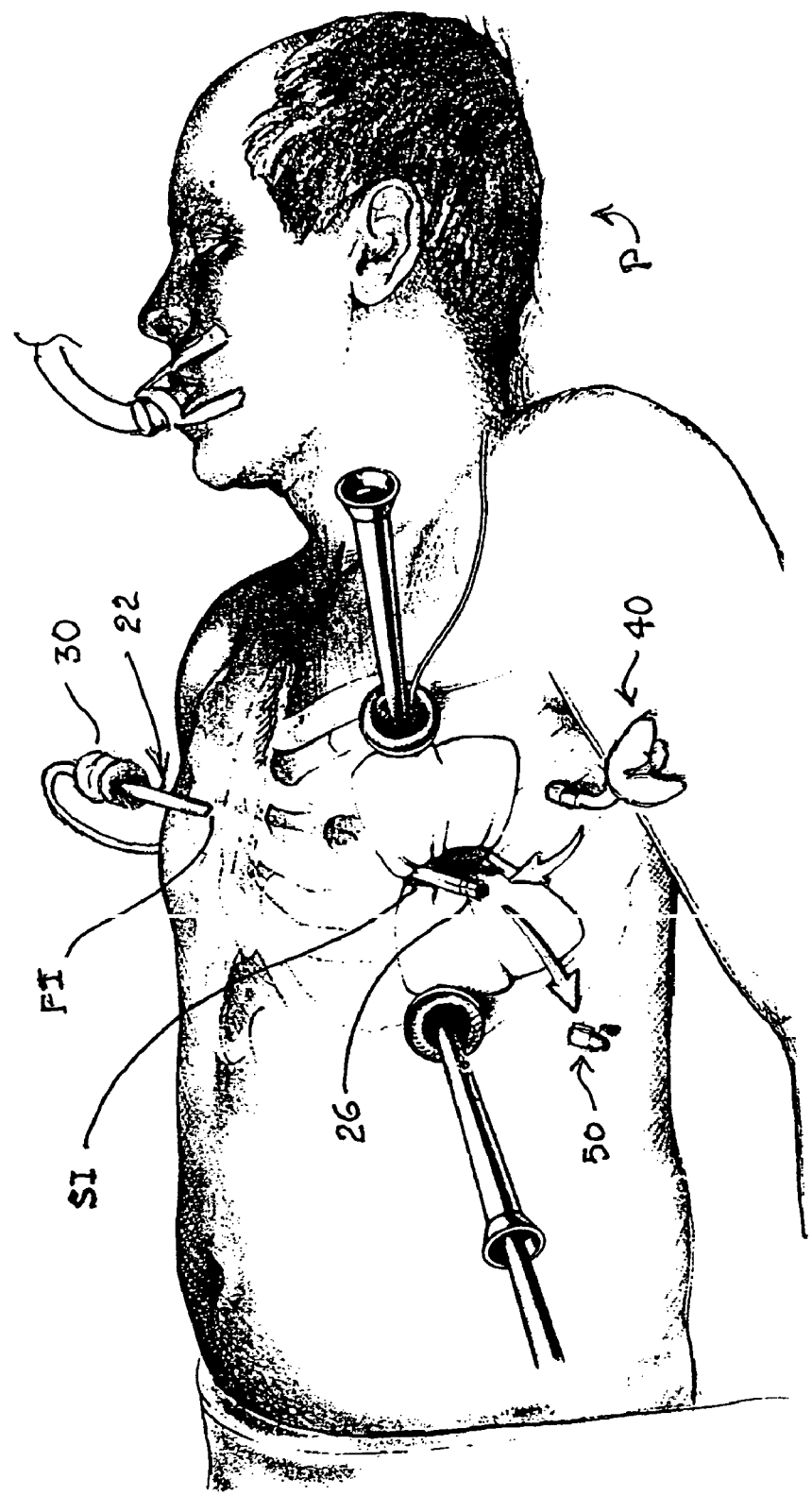
FIG. 5 is a schematic view of the system of FIG. 1 in relation to a patient illustrating obtaining access to the thoracic cavity and heart through at least first and second incisions and directing the shaft body distal end through the second incision where the blunting element is detached and the suction head is attached.
Figure 6:
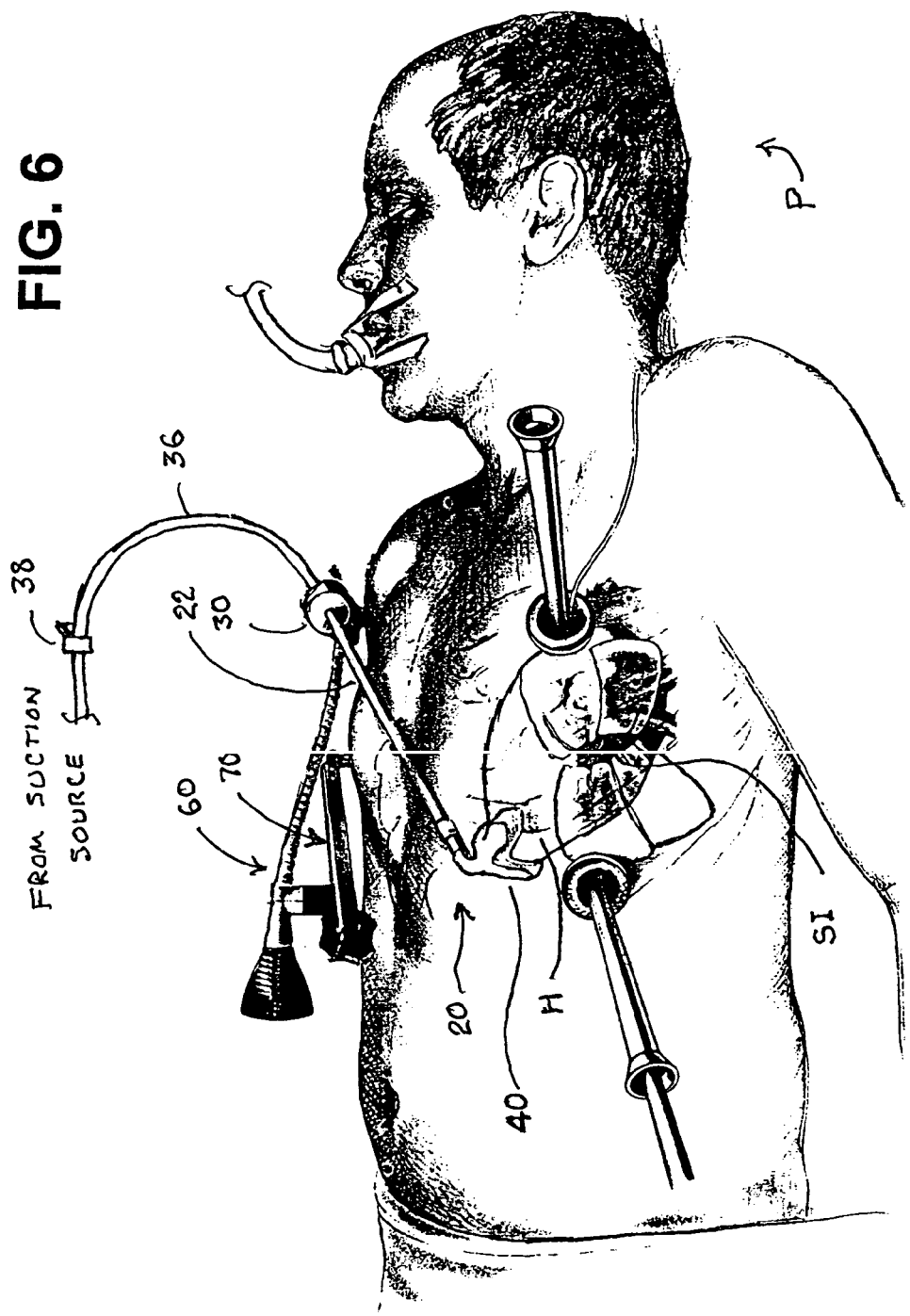
FIG. 6 is a schematic view of the system of FIG. 1 deployed to apply suction to the apex of the heart to lift and position the heart so that a desired site of the heart is exposed for a medical procedure conducted through the second incision.
Figure 7:
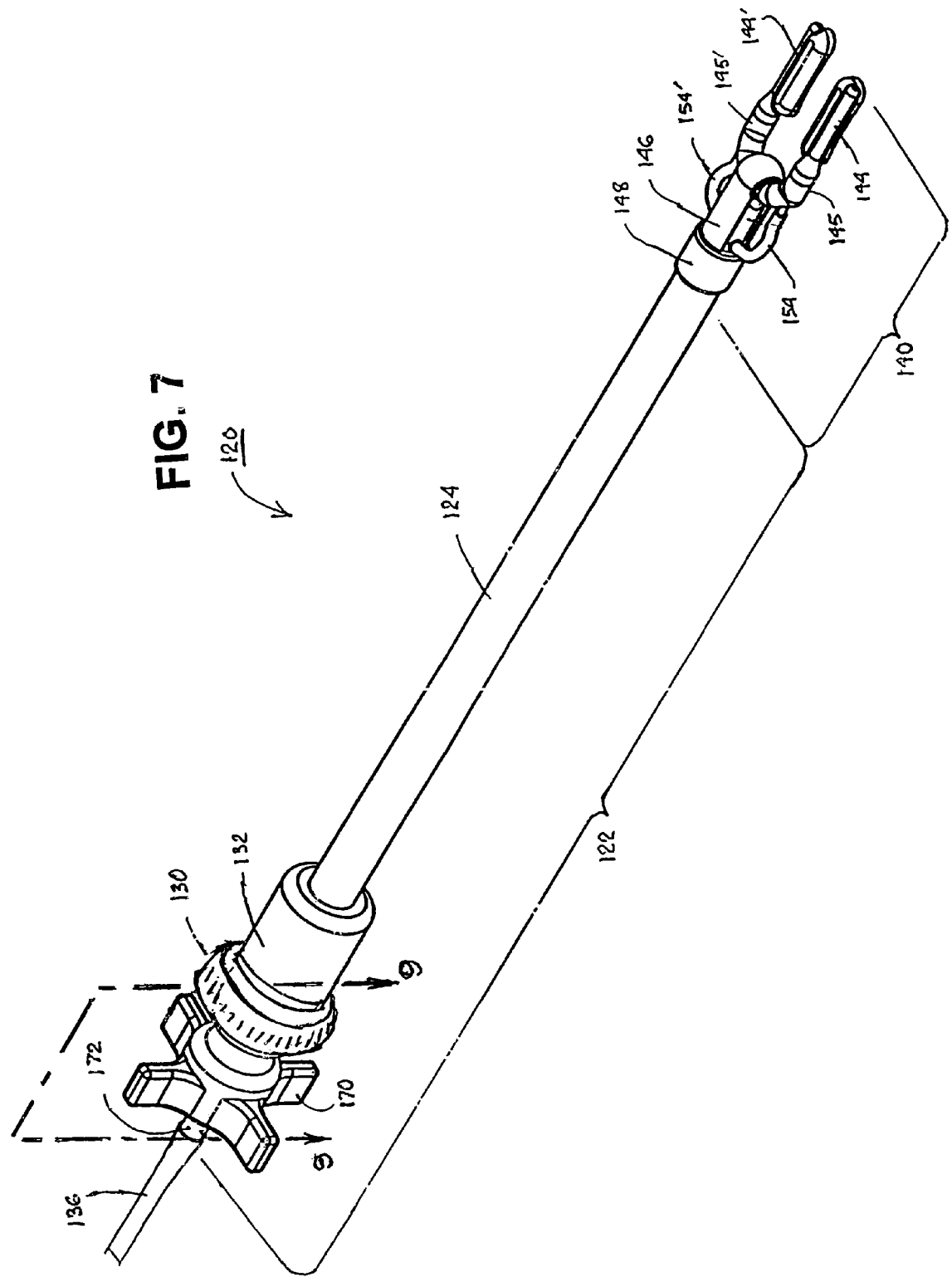
FIG. 7 is a perspective view of a second embodiment of a suction-assisted, tissue-engaging device adapted to be employed with the articulating arm and a support rail as illustrated in FIGS. 1, 5, and 6 particularly to stabilize a region of the heart to perform a medical procedure through the second incision.
Figure 8:
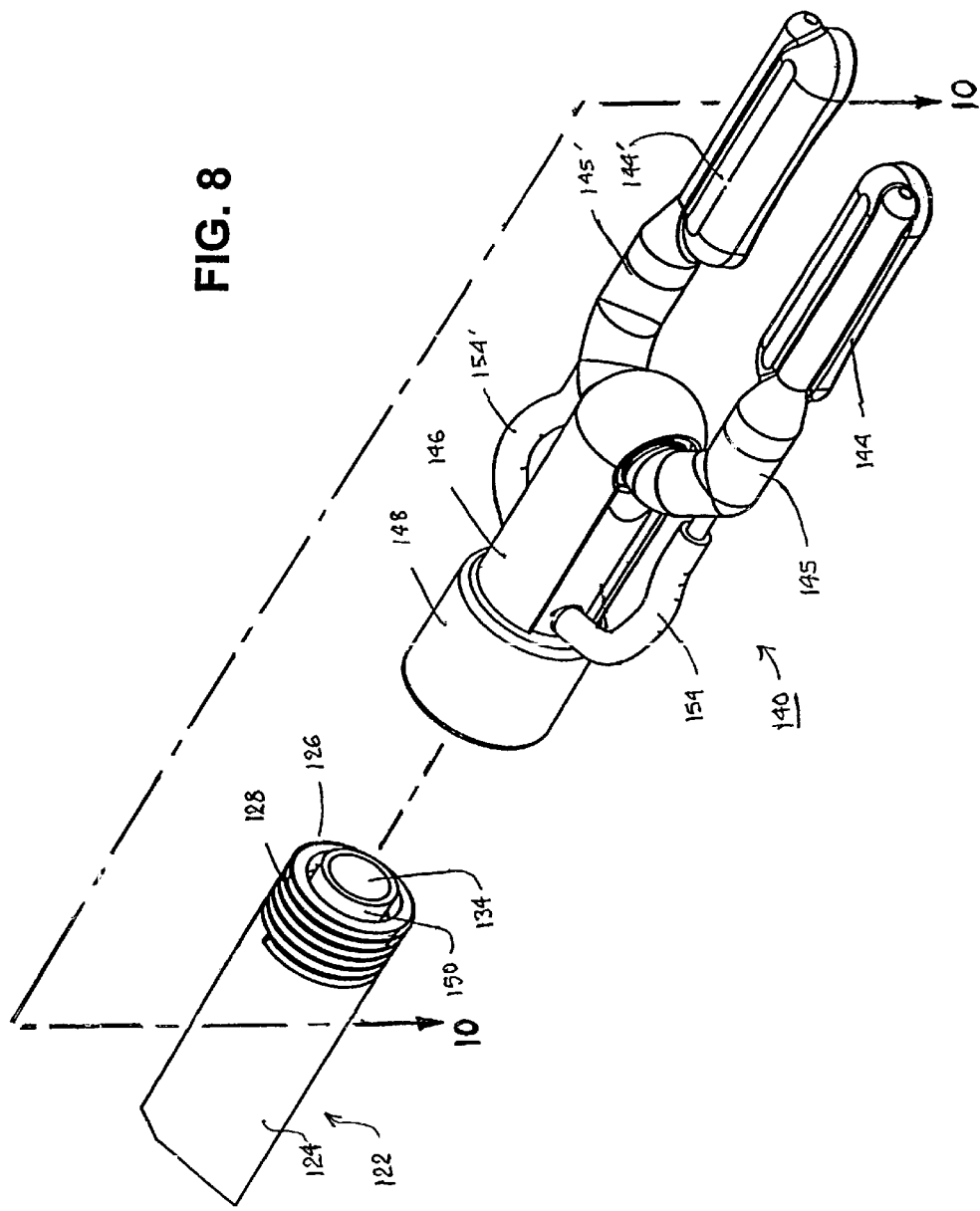
FIG. 8 is a perspective view of the fastener coupling the shaft body distal end with the suction head of the suction-assisted, tissue-engaging device of FIG. 7.

The system 10 of a first embodiment of the present invention is depicted in FIGS. 1-6 and comprises a suction-assisted tissue-engaging device 20, an articulating support arm 60, and a rail 70 that are assembled for operative use as shown in FIG. 6. The suction-assisted tissue-engaging device 20 further comprises first and second portions that can be attached together to apply suction to tissue or detached from one another to facilitate introduction or removal from a body cavity in the course of a medical procedure.

The first portion of the suction-assisted tissue-engaging device 20 is an elongated shaft 22 having a shaft body 24 extending between a proximal shaft handle 30 and shaft body distal end 26 and a shaft body diameter facilitating introduction through a minimally invasive first incision. A shaft body fastener element at the shaft body distal end 26 comprises a spiral thread 28. The proximal shaft handle 30 is enlarged to enable the user to grasp it outside the first incision and manipulate the elongated shaft body 24 in the manner described with reference to FIGS. 5 and 6. A clamp section 32 of proximal shaft handle 30 is shaped to be engaged by support arm 60. A shaft suction lumen 34 extends from a distal lumen end opening at the shaft body distal end 26 to a proximal fitting of proximal shaft handle 30 that is coupled to a flexible vacuum hose or line 36 adapted to be coupled to a vacuum source provided in an operating room that preferably provides a negative pressure of about 400 mm Hg. A stopcock 38 is provided in the suction tube 36 to provide or interrupt suction to the shaft suction lumen 34.

The second portion of the suction-assisted tissue-engaging device 20 comprises a suction member or head 40 that is configured to engage body tissue and function in this embodiment as an organ positioner, particularly a heart positioner and that can be attached to or detached from the shaft body distal end 26 either manually or with a tool. The suction head 40 comprises a suction pad 42 and a head shaft 46 supporting the fastener nut 48 at the head shaft proximal end 49 and enclosing a head suction lumen that extends into suction channels of a suction pad 42. The head shaft 46 is formed having a 90° angle distal segment 47, and suction pad 42 is supported at the distal end of the head shaft segment 47. The head shaft 46 can be made bendable in the 90° angle segment 47 so that the user can adjust the angle. Suction is applied to body tissue contacting suction ports (not shown) of the suction pad 42 from a vacuum source coupled to the suction tube 36 through the shaft suction lumen 34 and the head suction lumen extending through head shaft 46 to the suction ports.

The suction pad 42 can take any of the shapes of and incorporate any of the features of the suction pads employed in the above-referenced Starfish™ heart positioner and/or as disclosed in the above-referenced commonly assigned Publication No. 2002/0095067 having a plurality of legs, e.g., two to four legs. The illustrated suction pad 42 has three legs 44, 44', 44" that diverge outward in a generally starfish-shaped configuration. The legs 44, 44', 44" preferably are generally arcuate, curving downwardly away the head shaft distal end 47 to the free ends of the legs 44, 44', 44".

Preferably, the suction pad 42 and the legs 44, 44', 44" are formed integrally of substantially transparent or translucent medical grade silicone or thermoplastic elastomeric material (e.g., polyurethane). The material selected most preferably has a low durometer so that the suction pad 42 tends to conform to the surface of the heart and to flex to help seal against the heart to maintain the vacuum in the internal vacuum channels. The suction pad 52 is preferably sufficiently flexible such that the suction pad 52 draws down toward the surface of the heart more than the surface of the heart is pulled into the suction ports and channels.

In this embodiment, a separate blunting element 50 is provided as a third portion of the suction-assisted tissue-engaging device 20. The blunting element 50 is bullet-shaped having a blunt distal tip 52 and a proximal lumen having a female spiral thread 54. The blunting element 50 is attached to the shaft body distal end 26 so that the shaft body 24 can be advantageously manipulated within the body cavity without causing undesirable tissue damage. The blunting element 50 is detached from the shaft body distal end to enable attachment of the suction head 40 to the shaft body distal end 26 but can be reattached after the suction head 40 is detached to facilitate withdrawal of the elongated shaft body 22.

Optionally, the blunting element 50 can incorporate one or more sensors, electrodes, cameras, fiber optics, ports and/or orifices that are used during introduction into the body cavity, e.g., the thoracic cavity. In such a case, the suction tube 36 can be disconnected from the fitting at shaft handle 30, and tubing or electrical cable connected to the blunting element can be routed through the shaft body lumen 34 to external equipment. The shaft 20 may be packaged with the blunting tip installed to the shaft body distal end 26 in this configuration for use during introduction through the first incision and into the body cavity. The tubing or electrical cable can be withdrawn through the shaft body lumen 34 when the blunting element 50 is detached from the shaft body distal end 26.

In this embodiment, the fastener that is provided to selectively attach and detach one of the suction head 40 and the blunting element 50 to or from the shaft body distal end comprises a shaft body fastener element that can be coupled with a blunting element fastener element or to the suction head fastener element. The shaft body fastener element comprises the male spiral thread 28 at the shaft body distal end 26, the suction head fastener element comprises a female spiral thread of a rotatable fastener nut 48 of the suction head 40, and the blunting element fastener element comprises a female spiral thread 54 of a blunting element 50. The fastener can alternatively be formed as a bayonet fastener or a snap lock, a ball lock, or a push-pull luer lock or the like.

In accordance with one method of the present invention, the patient P is prepared for surgery and the first and second incisions FI and SI are made as shown in FIG. 5. The first incision FI may be made through the skin at a sub-xiphoid location, for example, and the second incision SI may be made as a left lateral small thoracotomy. As depicted in FIGS. 5 and 6 further trocar sieeves or ports are introduced through additional incisions for introducing instruments usable in the medical procedure into the thoracic cavity, and the soft tissue retractors are shown to maintain the small thoracotomy, second incision SI open.

The blunting element 50 is fastened to the shaft body distal end 26, and the shaft body 22 is inserted through the first incision FI into the thoracic cavity. The blunting element 50 can be detached from the shaft body distal end 26 by use of a wrench introduced through the second incision SI to unscrew it from the spiral thread 28 and can be removed from the thoracic cavity through the second incision SI. Similarly, the suction head 40 can be passed through the second incision SI and the nut 48 can be screwed onto the spiral thread 26 employing a wrench. The nut 48 can be unscrewed from the spiral thread 26 employing the wrench when the medical procedure is completed so that the suction head 40 can be withdrawn through the second incision SI and the shaft body 22 can be withdrawn through the first incision FI.

In a preferred method of the present invention illustrated in FIG. 5, the shaft handle 30 is manipulated to pass the shaft body distal end 26 out of the thoracic cavity through the second incision SI. The blunting element 50 is manually detached from the shaft body distal end 26 outside the body. The suction head 40 is then manually attached to the shaft body distal end 26 outside the patient's body to assemble the suction-assisted tissue-engaging device 20. The shaft handle 30 is again manipulated to bring the suction head 40 through the second incision SI into the thoracic cavity to apply suction to the heart to position the heart for the medical procedure to be performed using the second incision SI. When the medical procedure is completed, the shaft handle is again manipulated to push the suction head 40 through the second incision SI. The nut 48 can be manually unscrewed from the spiral thread 26 to remove the suction head 40 and allow the shaft body 22 to be withdrawn through the first incision FI.

The suction-assisted tissue-engaging device 20 is preferably attached prior to engaging the heart with suction as shown in FIG. 6 to a support that can be employed to maintain the elongated shaft 20 in an operative vector that is arrived at when the desired position is achieved for the duration of the medical procedure conducted through the second incision SI. In a preferred embodiment, the support comprises the elongated, articulating, support arm 60 having an arm distal end that can be attached to and detached from the elongated shaft 20 and an arm proximal end that can be attached to and detached from a fixed reference point. The fixed reference point preferably comprises the frame of the operating table or a rigid rail 70 attached to the operating table frame.

Figure 1:
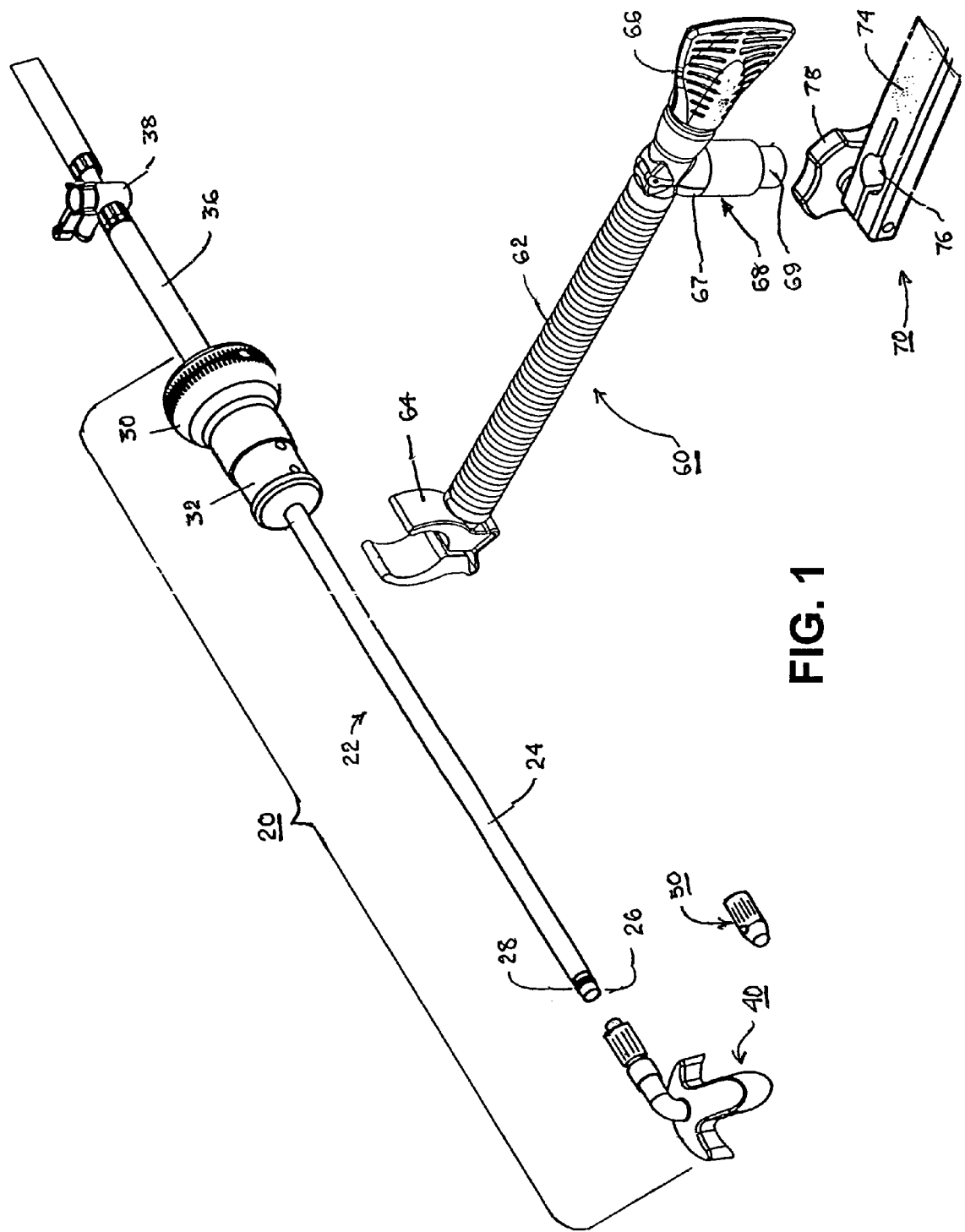
FIG. 1 is a partial perspective view of the components of a suction-assisted, tissue-engaging system comprising a suction-assisted, tissue-engaging device comprising an elongated shaft and a detachable suction head, an articulating arm, and a support rail in accordance with the first embodiment of the present invention.
Figure 2:
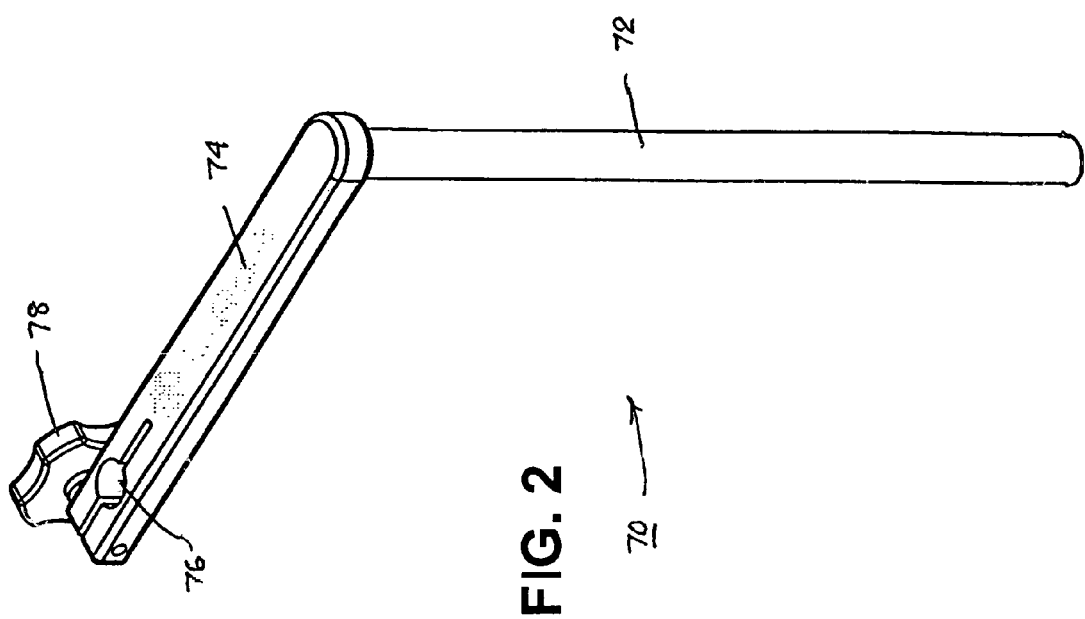
FIG. 2 is a perspective view of the support rail of FIG. 1.

The support shaft, handle or arm 60 shown in FIGS. 1 and 6 is preferably of the type that can readily be changed between a flexible or articulating condition or state and a rigid condition or state. For example, the articulating support arm 60 may comprise a plurality of articulating links 62 strung over an internal cable and extending between the distal arm clamp 64 and a proximal clamping mechanism 68. The internal cable extends axially within the articulating links 62 from a distal attachment at the distal clamp 64 through the length of the articulating support arm 60 to a proximal knob 66. The proximal knob 66 can be rotated in one direction to release tension on the cable so that a curve or bend can be formed along the length of the support arm 60 by manipulating the articulating links 62. The proximal knob 66 can then be rotated in the opposite direction to tension the cable, thereby drawing the articulating links 62 together to lock them into a shaped position. Each articulating link 62 has opposite ends, one of which is concave and the other of which is convex (e.g., hemispherical). The convex end of one articulating link 62 fits into the concave end of the adjacent articulating link 62, and allows the articulating links 62 to articulate relative to one another if the central cable has not been tensioned to lock the articulating links 62 together. The articulating links 62 can have a uniform cross section or the articulating links 62 closer to the distal clamp 64 can have a smaller cross section than the articulating links 62 closer to the proximal knob 66 and clamping mechanism 68. A suitable articulating mechanism could be similar to the type used in the above referenced Octopus 3™ tissue stabilization and the Starfish™ heart positioner. See, also, the articulating arm mechanisms disclosed in the above-referenced '311; '284, and '378 patents, the pending application Ser. No. 09/678,203, the Publication No. 2002/0095067, and the EP 0 993 806 publication.

The clamping mechanism 68 of the articulating support arm 60 comprises a turret 67 and a post 69 that is adapted to be coupled to the mounting rail 70 that is adapted to be attached to the operating table or another stable structure to provide a stable platform supporting the articulating support arm 60. The distal clamp 64 is also coupled to the internal cable, and is tightened when the proximal knob 66 is rotated to stiffen the articulating links 62.

The mounting rail 70 comprises a post 72 adapted to be clamped by clamps (not shown) to the frame of the operating table to extend vertically and an extension arm 74 that extends from the upper end of post 72 horizontally over the patient. The post 72 can be adjusted vertically to dispose the extension arm 74 horizontally over the patient at a desired distance from the patient's chest. The extension arm 74 has a slot 76 shaped to receive the post 69 of turret 67 and a knob 78 coupled to a shaft bridging the slot 76 and that can be rotated to compress the slot 76 around post 69.

Thus, the mounting rail 70 can be coupled to the operating table, and the articulating support arm 60 can be coupled to the mounting rail 70 so that the articulating support arm is fixed to a reference position. In use of the system as depicted in FIG. 6, the clamp section 32 of the shaft 22 is fitted into the distal clamp 64 of the articulating support arm 60 while the articulating arm 60 is in the flexible state.

After the suction head 40 is attached to the shaft body distal end 26, the user manipulates the shaft handle 30 and the heart to apply the suction pad 42 and legs 44, 44', 44" against the heart at a site that allows the heart to be engaged by the applied suction and held in a desired non-physiologic position. The shape of the legs 44, 44', 44" allow the suction pad 42 to be oriented to avoid placement over particular features of the heart anatomy, such as the cardiac arteries, or to avoid conflict with other devices employed in the medical procedure. When accessing various walls of the heart, the suction pad 42 can be preferably applied in one of two positions depending on the anatomy of the patient and the walls of the heart to be accessed. The first position is directly on the apex of the heart, which can be used for positioning for access to the lateral wall, posterior wall, or anterior wall of the heart. The second position is an off-apex position immediately adjacent to the apex. In particular, the suction pad 42 can be attached to the left ventricle immediately lateral to the apex of the heart. This particular off-apex position is especially useful for accessing the lateral wall in "apex under right hemisternum" position since even modest rightward movement of the apex greatly enhances exposure of proximal obtuse marginals. Thus, the suction pad 42 can be effectively attached to the heart not only on the apex but also to near-apex surfaces of the heart when that positioning would be desirable. The references herein to "near-apex", "near the apex of the heart" or the like includes application of the suction pad 42 onto the apex or onto other surfaces of the heart immediately adjacent to the apex.

Once a position of engagement is selected, a portion of the heart H is moved from its natural physiologic position to a non-physiologic position shown in FIG. 6 with one hand on the shaft handle 30 or the flexible articulating support arm 60 to move them about and the other hand inserted through the second incision S1 to support the heart H as it is positioned to expose the arteries or other structures to be repaired. As the suction pad 42 is applied to the heart H, the legs 44, 44', 44" may flex as required to conform to the surface of the heart.

Typically, the apex of he heart H is lifted upward as shown in FIG. 6. The stopcock 38 is opened to apply suction after positioning the heart and the suction pad 42 to cause the legs 44, 44', 44" to grasp the surface of the heart H. Preferably, the vacuum applied to the device should be a regulated vacuum that reaches about 400 mm Hg prior to positioning the heart H.

In this way, an operative vector defined by the axis of the elongated shaft body 22 extending through the first incision FI is defined. The proximal knob 66 is then rotated to render the articulating support arm 60 rigid to maintain the operative vector of the elongated shaft 20 stable and the heart H in the non-physiologic position. In this physiologic position, the heart H continues to beat and supply blood to the patient without marked deterioration in hemodynamic performance because the shape of the heart is not appreciably changed. In these medical procedures on the heart, it is also typically necessary to surgically open the pericardial sac surrounding the heart to expose the epicardium, and suction is applied through one of the described suction heads directly to the epicardium. The surgical exposure is preferably made through the second incision SI.

At the conclusion of the medical procedure, suction is discontinued, and the proximal knob 66 is rotated to render the articulating support arm 60 flexible and so that the elongated shaft 22 can be released from the articulating support arm 60. In the preferred method of the present invention, the shaft handle 30 is manipulated to pass the shaft body distal end 26 and attached suction member 40 out of the thoracic cavity through the second incision SI, and the suction head 40 is detached from the shaft body distal end 26 outside the patient's body. The shaft handle 30 is again manipulated to bring the elongated shaft body 24 back through the second incision SI into the thoracic cavity and to retract it from the thoracic cavity through the first incision FI.

The method and system as described above can be practiced employing alternative forms of the suction-assisted tissue-engaging device 20, e.g., the suction-assisted tissue engaging device 120 depicted in FIGS. 7-10. The suction-assisted tissue engaging devices 120 features a first portion comprising an elongated shaft 122 and a second portion comprising a detachable suction pod assembly or suction head 140 that, when assembled, can be used in the manner of the above-described Octopus 3™ tissue stabilizer to engage the heart and stabilize a region of the heart between the parallel suction pods. The suction-assisted tissue engaging device 120 can be fitted with the articulating support arm 60 and the mounting rail 70 and employed in a medical procedure as described above with reference to FIGS. 5 and 6, except that the heart is not repositioned from a physiologic position to a non-physiologic position in these embodiments.

The first portion of the suction-assisted tissue-engaging device 120 is an elongated shaft 122 having a shaft body comprising an outer tube 124 and an inner tube 150 extending between a proximal shaft handle 130 and shaft body distal end 126, the outer tube 124 having a shaft body diameter facilitating introduction through a minimally invasive first incision FI. The proximal shaft handle 130 is enlarged to enable the user to grasp it outside the first incision FI and manipulate the elongated shaft body in the manner described above with reference to FIGS. 5 and 6. A clamp section 132 of proximal shaft handle 130 is shaped to be engaged by support arm 60 as described above. A fastener comprising a male spiral thread 128 is provided at the shaft body distal end 126 for engagement with a female spiral thread of a rotatable fastener nut 148 of the suction head 140 or the female spiral thread 54 of the blunting element 50 depicted in FIG. 4. The fastener can alternatively be formed as a bayonet fastener or a snap lock, a ball lock, or a push-pull luer lock or the like.

Figure 9:
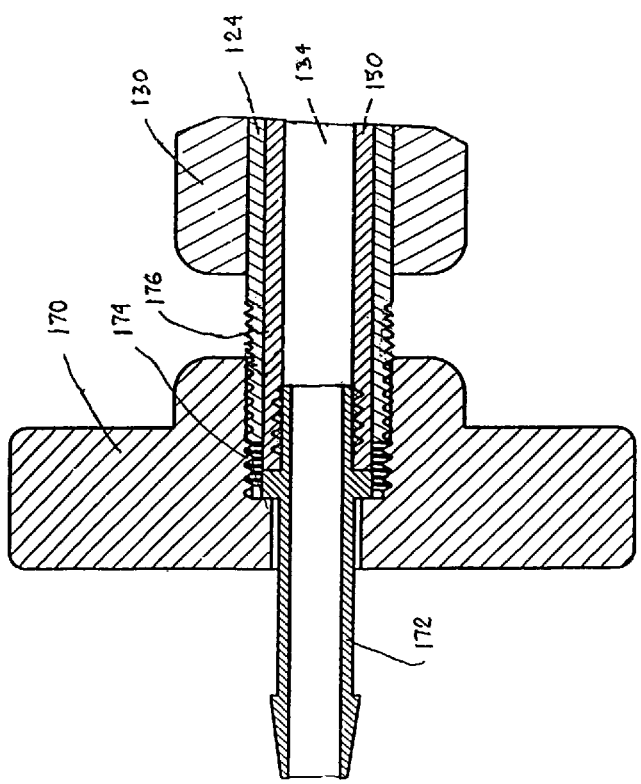
FIG. 9 is a cross-section view taken along lines 9-9 of FIG. 7 illustrating the actuator or knob at the shaft body proximal end for adjusting the distance between the pods of the suction head.
Figure 10:
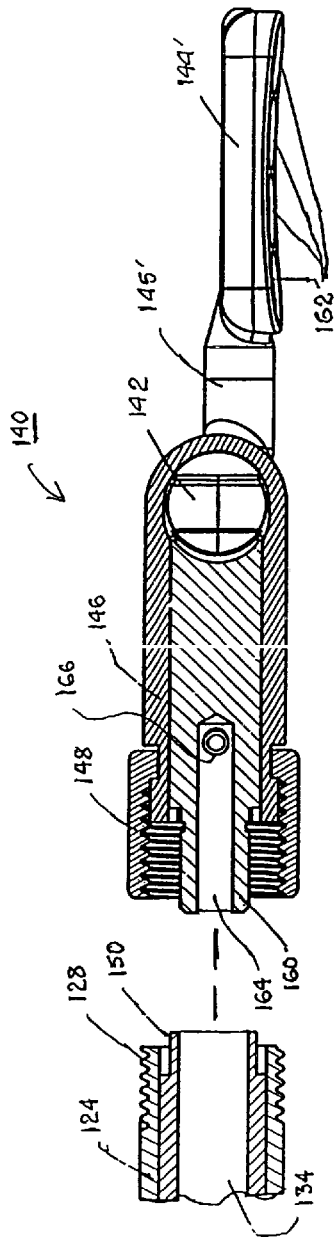
FIG. 10 is a cross-section view taken along lines 10-10 of FIG. 8 illustrating the fastener components of the suction head and the shaft body distal end.

The inner tube 150 disposed within the lumen of the outer tube 124 is attached at its proximal end to proximal fitting 172 and provides a shaft suction lumen 134 that extends from the distal lumen end opening at the shaft body distal end 126 to the proximal fitting 172. The proximal fitting 172 is coupled to a flexible vacuum hose or line 136 adapted to be coupled to a vacuum source provided in an operating room that preferably provides a negative pressure of about 400 mm Hg. A stopcock (not shown) is provided in the suction tube 136 to provide or interrupt suction to the shaft suction lumen 134. The inner tube 150 is also adapted to be moved axially within the lumen of the outer tube 124 by rotation of a remote actuator or knob 170 with respect to the outer tube 124. The knob 170 is coupled to the proximal end of the outer tube 124 through mating spiral threads 174 and 176 and abuts a flange 178 of the proximal fitting 172 as shown in FIG. 9. The rotation of the knob 170 in one direction causes the inner tube 150 to be moved distally within the lumen of the outer tube 124 and the axial movement applies force upon articulating elements in the suction head 140 to cause the suction pods 144 and 144' to be driven apart.

Turning to the suction head 140, it comprises a tubular housing 146 supporting a rotatable nut 148 having an interior spiral adapted to engage the spiral turn 128 at the shaft body distal end 126 to attach the suction head 140 to the shaft body distal end 126. A plunger 160 and a split ball mechanism 142 are disposed for axial movement in an interior chamber of the tubular housing 146. The split ball mechanism is coupled to support arms 145 and 145' that support the elongated pods 144 and 144' respectively. Distal movement of the plunger 160 compresses the split ball mechanism 142 and forces the support arms 145 and 145' to pivot outward and spread elongated suction pods 144 and 144', respectively, apart in a manner described for example in the above-referenced '629 patent.

The plunger 160 is formed with an axially extending bore 164 and cross-bore 166 that a vacuum is drawn through when the suction head 144 is attached to the elongated shaft 122 and the stopcock is opened. The cross-bore 166 extends to the lumens of suction tubes 154 and 154' that extend into the support arms 145 and 145' and to suction channels of the elongated suction pods 144 and 144', respectively. The configuration of the elongated suction pods 144 and 144' can take any of the configurations disclosed in the above-referenced '629 patent, for example.

When the suction head 144 is attached to the elongated shaft 122, a proximal portion of the plunger 160 is received in the suction lumen 134, and the distal end of the inner tube 150 bears against a proximal shoulder of the plunger 160. Therefore, rotation of the knob 170 in a direction moving the inner tube 150 distally, applies a force through the plunger 160 to move it distally against the resistance presented by the split ball mechanism 142 and forces the support arms 145 and 145' to pivot outward and spread elongated suction pods 144 and 144', respectively, apart.

In this embodiment, the suction head 140 can be attached and detached from the shaft body distal end 126 in the same manner as the suction head 40 is attached and detached from the shaft body distal end 26 as described above.

The method and system as described above can be practiced employing further alternative forms of the suction-assisted tissue-engaging device 20, e.g., the suction-assisted tissue-engaging device 220 depicted in FIGS. 11-24. The suction-assisted tissue engaging device 220 features a first portion comprising an elongated shaft 222 and a second portion comprising a detachable suction pod assembly or suction head 240, 340, 440 that, when assembled, can be used in the manner of the above-described Octopus 3™ tissue stabilizer to engage the heart and stabilize a region of the heart between the parallel suction pods. The suction-assisted tissue engaging device 220 can be fitted with the articulating support arm 60 and the mounting rail 70 and employed in a medical procedure as described above with reference to FIGS. 5 and 6, except that the heart is not repositioned from a physiologic position to a non-physiologic position in these embodiments.

In the further preferred embodiments illustrated in FIGS. 11-31, the first portion of the suction-assisted tissue-engaging device 220 is an elongated shaft 222 having a shaft body extending between a shaft body distal end 226 and a proximal shaft handle 230. The shaft body comprises an outer tube 224 and an inner rod 260 extending through a shaft lumen 238, the outer tube 224 having a shaft body diameter facilitating introduction through a minimally invasive first incision FI. The proximal shaft handle 130 is enlarged to enable the user to grasp it outside the first incision FI and manipulate the elongated shaft body in the manner described above with reference to FIGS. 5 and 6. A clamp section 232 of proximal shaft handle 230 is shaped to be engaged by support arm 60 as described above.

In these embodiments, the shaft fastener element extends through the shaft body from a shaft fastener proximal end at the shaft handle 230 to a shaft fastener distal end, and the shaft fastener is adapted to be moved to a disengage position to receive or release the suction head fastener element and to an engage position fixedly attaching the suction head to the shaft body distal end. The shaft fastener element can be manipulated through the shaft body lumen from the shaft handle 230 to engage or release the suction head 240 shown in detail in FIGS. 16-19 or the suction heads 340 and 440 depicted in FIGS. 23 and 24. The shaft fastener element comprises a distal latch or hook 250 attached to the distal end of the elongated rod 260, a toggle 270 coupled to the proximal end of the elongated rod 260 disposed at the proximal end 234 of the proximal handle 230, and a laterally extending slot 228 in the shaft body distal end 226 as shown in FIGS. 11, 12, and 21.

A slot or notch 255 is formed in the distal hook 250 that cooperates with is adapted to engage a suction head fastener element. The suction head fastener element comprises a bridge 246 of the suction head 240 shown in FIGS. 14-21 or a bridge 346, 446, 546, 646, 746, and 846 of the suction head embodiments shown in respective FIGS. 23, 24, 25, 26, 27, and 28 and described further below that fit into the notch 255 and bear against the laterally extending slot 228 in the shaft body distal end 226.

The distal hook 250 at the shaft body distal end 226 is preferably blunted so that the shaft body can be advantageously advanced through the first incision FI from a skin incision into the body cavity and out of the second incision SI without damaging tissue. As shown in FIG. 21, the distal hook 250 is shaped and dimensioned to fit within the shaft lumen 238 with a distal blunting element 252 projecting out of the shaft lumen end opening particularly when the suction head 240 or 340 is detached as shown in FIG. 15. The distal end of rod 260 is fitted into a proximal socket 256 of hook 250 and attached to distal hook 250 by a pin 262 extending laterally across the socket 256 and rod 260.

Figure 22:
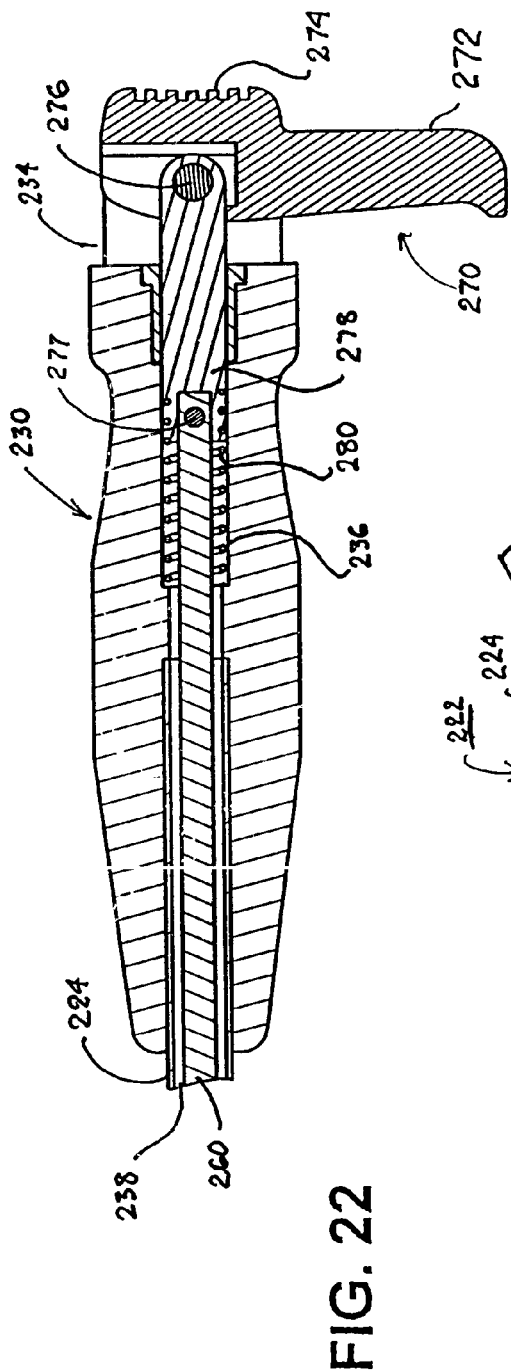
FIG. 22 is a cross-section view taken along lines 22-22 of FIG. 12 illustrating the toggle in the locked position.

As shown in FIG. 22, the toggle 270 comprises a toggle arm 272 and a toggle button 274, and the toggle 270 is mounted to a piston 278 within a chamber 236 of shaft handle 230 by a pin 276 extending laterally through the proximal end of piston 278 that is in turn coupled to the proximal end of rod 260 by laterally extending pin 277. The toggle arm 272 can be manipulated to rotate the toggle 270 between a neutral toggle position depicted in FIGS. 11 and 22 and a toggle locked position depicted in FIG. 12. As shown in FIG. 22, an internal spring 280 within chamber 236 of proximal handle 230 biases the toggle 270 and the rod 260 proximally. In this way, the hook 250 is retracted into the shaft lumen 238 as shown in FIGS. 11, 12, 15 and 21 in either of the locked or neutral toggle positions whether the suction head 240 or 340 or 440 is attached or is not attached. With the suction head 240 or 340 or 440 detached, the spring bias ensures that the distal blunting element 252 projects a short distance distally from the lumen distal end opening at shaft body distal end 226 as shown in FIG. 15. The toggle arm 272 can be rotated about pin 276 into the locked position depicted in FIG. 12 with the suction head 240 or 340 or 440 or 540 or 640 or 740 or 840 detached to blunt shaft body distal end 226 and minimize damage to the heart or other body tissue when the shaft body distal end 226 is moved about the thoracic cavity or out of the second incision SI as illustrated in FIG. 5.

The spring bias presented by spring 280 can be overcome by depressing the toggle button 274 distally as shown in FIG. 13 into an advanced position to move the hook 250 distally to expose the notch 255 so that the bridge 246 of the suction head 240 or the bridge 346 of the suction head 340 or the ring 446 of the suction head 440 can be inserted into or removed from notch 255 and slot 228 as also shown in FIG. 14.

Figure 31:
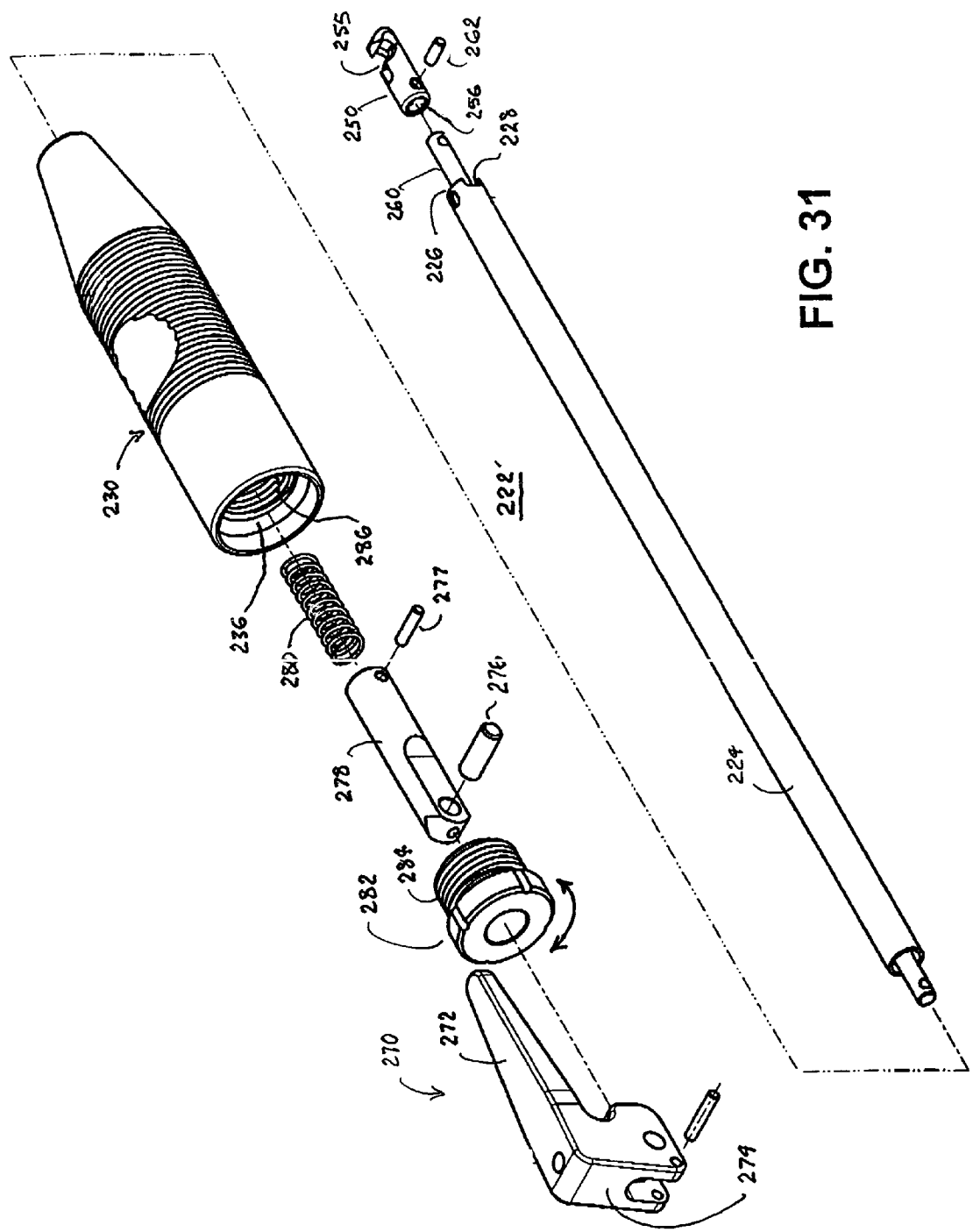
FIG. 31 is a perspective view of a still further embodiment of the elongated shaft illustrated in FIGS. 11-15 and 21-22 and the elongated shaft illustrated in FIG. 30.

A further embodiment of a an elongated shaft 222' is depicted in FIG. 31 and corresponds generally to elongated shaft 222 as described above. In this variation, an adjustable tubular spacer 282 having a screw thread 284 is fitted over the piston 278 and screwed onto threads 286 within chamber 236. The spacer 282 is thereby fitted between the toggle 270 and the shaft handle 230. The spacer 230 can be rotated by the user to selectively adjust the advanced, locked, and neutral positions of the distal hook 250. Various other connector parts are depicted in FIG. 31.

The first suction head 240 that can be attached as the second portion to the elongated shaft 222 or 222' is depicted in detail in FIGS. 11-14, 16-19 and 21. Suction head 240 comprises the U-shaped bridge 246 functioning as the suction head fastener element that can be engaged within the notch 255 and the slot 228 as described above and that supports the elongated suction pods 244 and 244' spaced apart generally in parallel with one another at supports 245 and 245', respectively. The elongated suction pods 244 and 244' are formed with suction nozzles 254 and 254', respectively, extending rearward or proximally and that enable application of suction through suction channels within the suction pods 244 and 244' when suction tubes are coupled to the suction nozzles 254 and 254'. The suction channels within the suction pods 244 and 244' extend to suction ports 248 and 248' respectively formed through suction pod tissue engaging surfaces 242 and 242', respectively.

Figure 23:
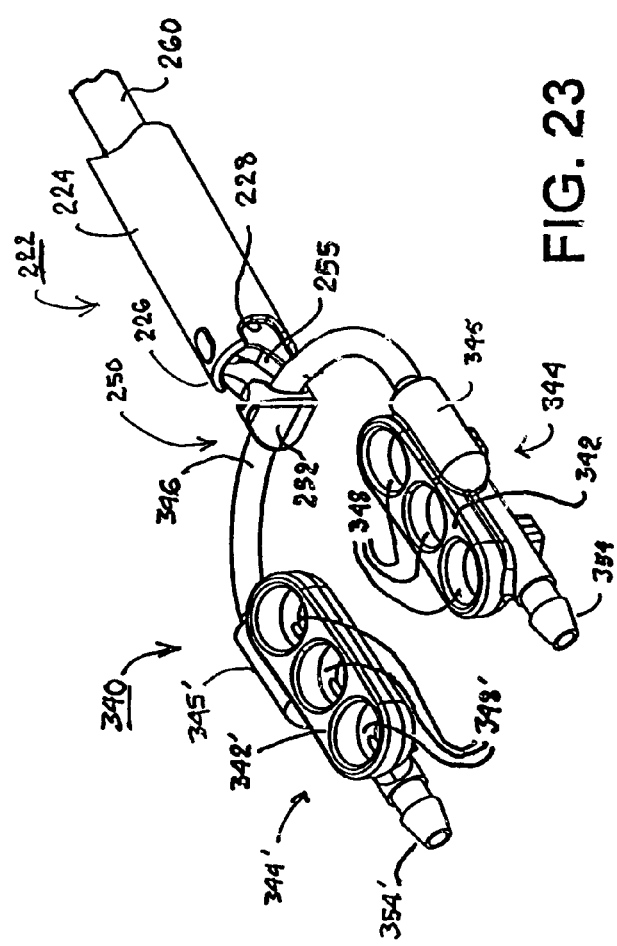
FIG. 23 is a partial perspective view of a fourth embodiment of a suction head coupled with the elongated shaft of FIGS. 11-15 and adapted to be employed with the articulating arm and a support rail as illustrated in FIGS. 1, 5, and 6 particularly to stabilize a region of the heart to perform a medical procedure through the second incision.

The second suction head 340 that can be attached as the second portion to the elongated shaft 222 or 222' is depicted in FIGS. 23 and 29. Suction head 340 also comprises a U-shaped bridge 346 functioning as the suction head fastener element that can be engaged within the notch 255 and the slot 228 as described above and that supports the elongated suction pods 344 and 344' spaced apart generally in parallel with one another at supports 345 and 345', respectively. The elongated suction pods 344 and 344' are formed with suction nozzles 354 and 354', respectively, extending forward or distally and that enable application of suction through suction channels within the suction pods 344 and 344' when suction tubes are coupled to the suction nozzles 354 and 354'. The suction channels within the suction pods 344 and 344' extend to suction ports 348 and 348' respectively formed through suction pod tissue engaging surfaces 342 and 342', respectively.

Sutures may be used to attach or position epicardial tissue relative to the elongated suction pods 344 and 344" to enhance the stabilization function of the invention and or to position epicardial tissue or the target vessel of an anastomosis. As shown in FIG. 29, suture holding members 360 and 362 extending from the elongated suction pod 344, and suture holding members 360' and 362' extending from the elongated suction pod 344' are used to hold sutures to stabilize and position tissue surrounding the site of an anastomosis and the target cardiac artery. Sutures may be placed or passed through the epicardial tissue (not shown) and fixed to the suture holding members 360, 362 and 360' 362' by passing the sutures through slots or passages of the suture holding members 360, 362 and 360' 362' that frictionally engage the sutures. The sutures then effectively position several points on the surface of the beating heart in fixed relationship to elongated suction pods 344 and 344'.

In addition, one or more sutures may be passed through the myocardium around a target vessel positioned between the elongated suction pods 344 and 344' and inserted through a pair of the slots of the suture holding members 360, 362 and 360' 362'. The surgeon can tighten or loosen the sutures extending around the target vessel to control blood flow through the target vessel, and the tightened or loosened state is maintained by the frictional engagement of the sutures by the suture holding members 360, 362 and 360' 362'. It will be understood that such suture holding members can also be incorporated in the suction heads 140, 240, and 440

Figure 24:
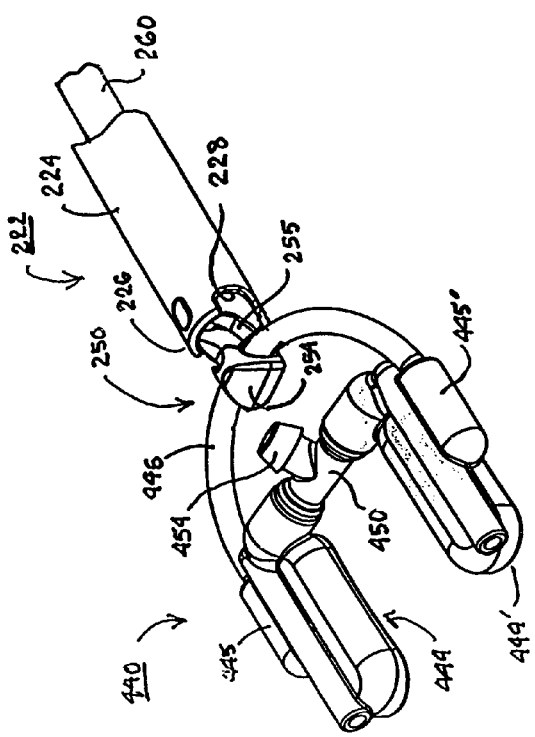
FIG. 24 is a partial perspective view of a fifth embodiment of a suction head coupled with the elongated shaft of FIGS. 11-15 and adapted to be employed with the articulating arm and a support rail as illustrated in FIGS. 1, 5, and 6 particularly to stabilize a region of the heart to perform a medical procedure through the second incision.

The third suction head 440 that can be attached as the second portion to the elongated shaft 222 or 222' is depicted in FIG. 24. Suction head 440 also comprises a U-shaped bridge 446 functioning as the suction head fastener element that can be engaged within the notch 255 and the slot 228 as described above and that supports the elongated suction pods 444 and 444' spaced apart generally in parallel with one another at supports 445 and 445', respectively.

The elongated suction pods 444 and 444' are joined together by T-shaped suction tube 450 that is formed with a single suction nozzle 454. The suction nozzle 454 can extend rearward or distally as shown in FIG. 24 or can extend forward or distally or in any other convenient direction for attachment to a suction tube, e.g., suction tube 36 of FIG. 6. The suction applied through the nozzle 454 and suction tube 450 that enable application of suction through suction channels within the suction pods 444 and 444'. The suction channels within the suction pods 444 and 444' extend to suction ports 448 and 448' respectively formed through suction pod tissue engaging surfaces 442 and 442', respectively.

Figure 25:
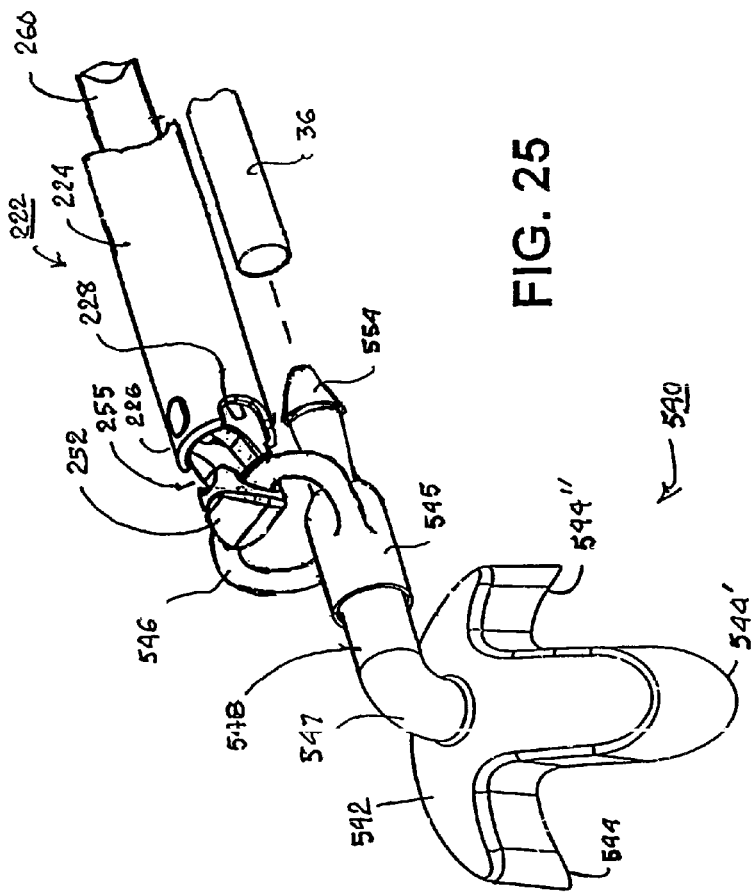
FIG. 25 is a partial perspective view of a sixth embodiment of a suction head coupled with the elongated shaft of FIGS. 11-15 and adapted to be employed with the articulating arm and a support rail as illustrated in FIGS. 1, 5, and 6 particularly to position the heart to perform a medical procedure through the second incision.

It will be appreciated that the elongated shaft 222 depicted in FIGS. 11-15 and 21-24 or elongated shaft 222' depicted in FIG. 31 can also be employed with suction head 540 depicted in FIG. 25 or with suction head 640 depicted in FIG. 26 that are configured in shape to function and to be used in the same manner as the suction head 40 described above in reference to FIGS. 1-6. The suction heads 540 and 640 depicted in FIGS. 25 and 26 comprise a suction pad 542, 642 and a head shaft 548, 648 enclosing a head suction lumen that extends into suction channels of suction pad 542, 642. The suction head fastener element of the suction head 540 comprises a tube 545 surrounding the head shaft 548 and a ring-shaped bridge 546 extending outward of tube 545 adapted to be received in the notch 255 of hook 254. The tube 545 can either be fixed to the head shaft 548 or the head shaft 548 can be loosely received within the lumen of tube 545 to allow the suction pad 542 to be moved with respect to the shaft body distal tip 226. The suction head fastener element of the suction head 640 comprises a ring-shaped bridge 646 extending outward of the suction pad 642 adapted to be received in the notch 255 of hook 254. The suction head 540 or 640 can be attached as the second portion to the elongated shaft 222 or 222' by insertion of the ring-shaped bridge 546 or 646 into the notch 255 to bear against the slot 228 as described above in reference to FIGS. 11-13.

In the suction heads 540 and 640, the head shaft 548, 648 extends proximally to a suction tube nozzle 554, 654 adapted to be coupled to a suction tube 36, but the head shaft could extend distally in the manner of the suction head 340 to locate the nozzle 554. 654 distal to the suction pad 542, 642. The head shaft 548, 648 is formed having a 90° angle in head shaft segment 547, 647, and suction pad 542, 642 is supported at the distal end of the head shaft distal segment 547, 647. The head shaft 548, 648 can be made bendable in the 90° angle distal segment 547, 647 so that the user can adjust the angle. Suction is applied to body tissue contacting suction ports (not shown) of the suction pad 542, 642 from a vacuum source coupled to the suction tube 36 through the suction nozzle 554, 654 and the head suction lumen extending through head shaft 546, 646 to the suction ports.

The suction pad 542, 642 can take any of the shapes of and incorporate any of the features of the suction pads employed in the above-referenced Starfish™ heart positioner and/or as disclosed in the above-referenced Publication No. 2002/0095067 having a plurality of legs, e.g., two to four legs. The illustrated suction pad 542, 642 has three legs 544, 544', 544" or 644, 644', 644" that diverge outward in a generally starfish-shaped configuration. The legs 544, 544', 544" or 644, 644', 644" preferably are generally arcuate, curving downwardly away the head shaft distal end 547, 647 to the free ends of the legs 544, 544', 544" or 644, 644', 644".

It will also be appreciated that the elongated shaft 222 depicted in FIGS. 11-15 and 21-24 or elongated shaft 222' depicted in FIG. 31 can also be employed with conical suction head 740 depicted in FIG. 27 or with conical suction head 640 depicted in FIG. 28 to be used in the same manner as described above in reference to FIGS. 1-6. The suction heads 740 and 840 depicted in FIGS. 27 and 28 comprise a conical suction pad 742, 842 and a head shaft 748, 648 enclosing a head suction lumen that extends from a suction nozzle 754, 854 into suction channels of the suction pad 542, 642. It will be understood that the conical suction pad 742, 842 is resilient and flexible and includes an array of suction ports obscured in the views. The conical suction pad 742, 842 can take the form disclosed in the above-referenced PCT Publication WO 01/17437 A2.

The suction head fastener element of the conical suction head 740 comprises an elongated ring-shaped bridge 746 extending around and laterally away from the head shaft 748 and suction nozzle 754 to provide two loops that can be selectively received in the notch 255 of hook 254. The suction head fastener element of the conical suction head 840 comprises a ring-shaped bridge 846 extending away from the head shaft 848 to provide a single loop that can be selectively received in the notch 255 of hook 254. The suction head 740 or 840 can be attached as the second portion to the elongated shaft 222 or 222' by insertion of the ring-shaped bridge 746 or 846 into the notch 255 to bear against the slot 228 as described above in reference to FIGS. 11-13. Suction is applied to body tissue contacting suction ports (not shown) of the suction pad 742, 842 from a vacuum source coupled to the suction tube 36 through the suction nozzle 754, 854 and the head suction lumen extending through head shaft 746, 846 to the suction ports.

In the suction head 840, the head shaft 848 is formed having a 90° angle in head shaft segment 847, and suction pad 842 is supported at the distal end of the head shaft distal segment 847. The head shaft 848 extends proximally to a suction tube nozzle 854 adapted to be coupled to a suction tube 36, but the head shaft 848 could extend distally in the manner of the suction head 340 to locate the nozzle 854 distal to the conical suction pad 842. The head shaft 848 can be made bendable in the 90° angle distal segment 847, 647 so that the user can adjust the angle. It will be understood that the head shaft 748 can also be formed in the manner of head shaft 848.

Any of the suction pads 240, 340, 440, 540, 640, 740, and 840 can be attached to the distal fastener of the shaft 222 or 222' in the manner described above when the shaft distal end 226 and hook 250 are passed through the second incision S1 as shown in FIG. 5. The suction tube(s) can be attached to the proximally extending suction nozzles 254, 254' of suction head 240 or the distally extending suction nozzles 354, 354' of suction head 340 or the nozzles 454, 554, 654, 754 or 854 of respective suction heads 440, 540, 640, 740, or 840. The suction head 240 or 340 or 440 or 540 or 640 or 740 or 840 and the attached suction tube(s) 36 can then be drawn into the thoracic cavity through the second incision S1. Alternatively, it may be desirable to route the suction tube(s) 36 through the first incision FI or a further small incision and out of the thoracic cavity through the second incision SI for attachment to the proximally extending suction nozzles 254, 254' of suction head 240 or the distally extending suction nozzles 354, 354' of suction head 340 or nozzle or the nozzles 454, 554, 654, 754 or 854 of respective suction heads 440, 540, 640, 740, or 840. The suction head 240 or 340 or 440 or 540 or 640 or 740 or 840 is moved about the thoracic cavity to the site on the heart where suction is to be applied as described above. The choice of use of suction head 240 or 340 or 340 to stabilize a region or site of the heart may depend upon the preferred way of orienting the suction tubes in relation to the site.

The above-described embodiments of the suction heads 240, 340, 440, 540, 640, 740 and 840 and the elongated shaft 222 or 222' involve use of a separate suction tube 36 that is introduced through the first or second incisions FI and SI or a third incision of FIGS. 5 and 6 for example, and the coupling of the suction tube 36 to the suction nozzle or nozzles. As shown in FIG. 30, it will be understood that a vacuum could be drawn through the shaft lumen 238 depicted in FIGS. 21 and 22 through attachment of the suction tube 36 to a side port 264 extending from the shaft lumen 238 at or adjacent the proximal shaft handle 230. An opening 288 (shown in dotted lines) is formed through the wall of outer tube 224 proximal to socket 256 of hook 250 depicted in FIG. 21. A suction adaptor 290 having a proximal ring-shaped fitting 292 and two suction tubes 294 and 294' extend distally therefrom is depicted in FIG. 26. The ring-shaped fitting 292 can be slipped over the shaft body distal end 226 and moved proximally over outer tube 224 to fit over the opening 288 and seal it while the shaft body distal end 226 is within the thoracic cavity or after the shaft body distal end 226 is extended out through the second incision S2 as shown in FIG. 5. The free ends of the suction tubes 294 and 294' are fitted onto the nozzles 254 and 254', respectively, when the suction head 240 is attached to the elongated shaft 222 or 222' as described above.

It will be understood that the suction adaptor 290 can comprise only a single suction tube 294 attached to the single nozzle 454 of suction head 440 or the single nozzle 554 of suction head 540 or the single nozzle 654 of suction head 640 or the single nozzle 754 of suction head 740 or the single nozzle 854 of suction head 840 and variations thereof. Moreover, it will be understood that the suction adaptor 290 having one or two suction tubes 294 and 294' can be miniaturized and attached permanently to the outer tube 224 at or near the shaft body distal end 226.

All patents and publications referenced herein and the above-referenced Provisional No. 60/404,969 filed Aug. 21, 2002 and Provisional No. 60/424,243 filed Nov. 6, 2002 are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments.

In addition, it will be understood that specifically described structures, functions and operations set forth in the above-referenced patents can be practiced in conjunction with the present invention, but they are not essential to its practice. It is therefore to be understood, that within the scope of the appended claims, the invention may be practiced otherwise than as specifically described without actually departing from the spirit and scope of the present invention.

What is claimed is:

1. A method of performing a medical procedure on a body organ, accessed through first and second incisions into a body cavity comprising:

providing an elongated shaft having a shaft body extending between a proximal shaft handle and a shaft body distal end, the shaft body distal end supporting a shaft fastener element, providing a suction head having a suction pad adapted to be coupled to a source of suction to engage the body organ through the application of suction to the body organ and a suction head fastener element adapted to be attached to or detached from the shaft fastener element;

advancing the elongated shaft through both the first and second incision to dispose the shaft body distal end outside the body adjacent the second incision while the shaft handle is disposed outside the body adjacent the first incision;

attaching the suction head fastener element to the shaft fastener element to form a suction-assisted tissue-engaging device; positioning the suction pad of the suction head against the body organ;

applying suction through the suction pad to engage the body organ; and, performing the medical procedure on the body organ via the second incision.

2. The method of claim 1, wherein the positioning step further comprises: orienting the shaft body through the first incision into an operative vector in 3-D space for engagement of the suction head with the body organ; and rigidly maintaining the operative vector to enable performance of the medical procedure on the body organ.

3. A method of performing a medical procedure on a body organ, accessed through first and second incisions into a body cavity comprising:

providing an elongated shaft having a shaft body extending between a proximal shaft handle and a shaft body distal end, the shaft body distal end supporting a shaft fastener element, providing a suction head having a suction pad adapted to be coupled to a source of suction to engage the body organ through the application of suction to the body organ and a suction head fastener element adapted to be attached to or detached from the shaft fastener element;

advancing the elongated shaft through the first incision to dispose the shaft body distal end within the body cavity or inserted through both the first and second incision to dispose the shaft body distal end outside the body adjacent the second incision while the shaft handle is disposed outside the body adjacent the first incision;

attaching the suction head fastener element to the shaft fastener element to form a suction-assisted tissue-engaging device;

positioning the suction pad of the suction head against the body organ;

applying suction through the suction pad to engage the body organ;

performing the medical procedure on the body organ via the second incision; and further comprising upon completion of the medical procedure: discontinuing application of suction; repositioning the suction pad of the suction head away from the body organ; detaching the suction head fastener element from the shaft fastener element; and removing the shaft body from the chest cavity through the first incision.

4. The method of claim 3, further comprising coupling a blunting element to the shaft body distal end prior to advancing the shaft body through the first incision; and decoupling the blunting element from the shaft body distal end prior to attaching the suction head fastener element to the shaft fastener element.

5. The method of claim 3 wherein the shaft fastener element is shaped to blunt the shaft body distal end during advancing the shaft body through the first incision.

6. The method of claim 3, wherein the positioning step further comprises: orienting the shaft body through the first incision into an operative vector in 3-D space for engagement of the suction head with the body organ; and rigidly maintaining the operative vector to enable performance of the medical procedure on the body organ.

7. The method of claim 3, wherein: the shaft body comprises a shaft lumen extending from the shaft handle to the shaft body distal end; the shaft fastener element further comprises: an elongated rod extending through the shaft lumen from a rod proximal end and a rod distal end; a distal hook at the elongated rod distal end shaped to engage the suction head fastener element; and a toggle mounted to the shaft handle and coupled to the rod proximal end adapted to move between a neutral position, a locked position and an advanced position; the advancing step comprises moving the toggle to the neutral position to dispose the distal hook substantially within the shaft body distal end the attaching step comprises moving the toggle to the advanced position to expose the hook, fitting the suction head fastener element into the hook, and moving the toggle to the locked position; and the detaching step comprises moving the toggle to the advanced position to expose the hook, removing the suction head fastener element from the hook, and moving the toggle to the neutral position.

8. The method of claim 7, wherein the suction pad comprises first and second suction pods supported by the suction head fastener element to extend substantially in parallel and spaced apart from one another, and the suction applying step comprises applying suction through the suction pods to stabilize organ tissue between the first and second suction pods to facilitate performing the medical procedure upon the body organ employing the second incision.

9. The method of claim 8, wherein the first and second suction pods are elongated, and each comprise at least one suction port adapted to be applied against the body organ and a suction nozzle extending toward the shaft body distal end, and the suction applying step comprises attaching vacuum lines to the suction nozzles for application of suction to the body organ through the applied suction ports.

10. The method of claim 9, further comprising the step of extending the vacuum lines through the first incision.

11. The system of claim 8, wherein the first and second suction pods are elongated, and each comprise at least one suction port adapted to be applied against the body organ and a suction nozzle extending away from the shaft body distal end, and the suction applying step comprises attaching vacuum lines to the suction nozzles for application of suction to the body organ through the applied suction ports.

12. The method of claim 11, further comprising the step of extending the vacuum lines through the second incision.

13. The system of claim 8, wherein: the first and second suction pods are elongated, and each comprise at least one suction port adapted to be applied against the body organ; and a suction tube extends between the first and second suction ports, the suction tube supporting a suction nozzle; and the suction applying step comprises attaching a vacuum line to the suction nozzle for application of suction to the body, organ through the applied suction ports.

14. The method of claim 13, further comprising the step of extending the vacuum line through one of the first and second incision.

15. The method of claim 7, wherein the suction pad is shaped to conform anatomically to an area of the body organ to enable the body organ to be moved into and maintained in a non-physiologic position within the body cavity to facilitate performing the medical procedure upon the body organ employing the second incision.

16. The method of claim 3, wherein the suction pad is shaped to conform anatomically to an area of the body organ to enable the body organ to be moved into and maintained in a non-physiologic position within the body cavity to facilitate performing the medical procedure upon the body organ employing the second incision.

17. The method of claim 3, wherein: the suction pad comprises first and second suction pods supported by the suction head fastener element to extend substantially in parallel and spaced apart from one another; the suction head comprises a spreading mechanism that selectively spreads the first and second suction pods apart; and the suction applying step comprises: applying suction through the suction pods to grasp the organ tissue; and operating the spreading mechanism to spread the first and second suction pods apart to stretch the organ tissue between the first and second suction pods when suction is applied therethrough to the organ tissue to stabilize the organ tissue between the first and second suction pods to facilitate performing the medical procedure upon the body organ employing the second incision.

18. The method of claim 3, wherein the suction pad comprises first and second suction pods supported by the suction head fastener element to extend substantially in parallel and spaced apart from one another, and the suction applying step comprises applying suction through the suction pods to stabilize organ tissue between the first and second suction pods to facilitate performing the medical procedure upon the body organ employing the second incision.

19. The method of claim 18, wherein the first and second suction pods are elongated, and each comprise at least one suction port adapted to be applied against the body organ and a suction nozzle extending toward the shaft body distal end, and the suction applying step comprises attaching vacuum lines to the suction nozzles for application of suction to the body organ through the applied suction ports.

20. The method of claim 19, further comprising the step of extending the vacuum lines through the first incision.

21. The method of claim 18, wherein the first and second suction pods are elongated, and each comprise at least one suction port adapted to be applied against the body organ and a suction nozzle extending away from the shaft body distal end, and the suction applying step comprises attaching vacuum lines to the suction nozzles for application of suction to the body organ through the applied suction ports.

22. The method of claim 21, further comprising the step of extending the vacuum lines through the second incision.

23. The method of claim 18, wherein: the first and second suction pods are elongated, and each comprise at least one suction port adapted to be applied against the body organ; and a suction tube extends between the first and second suction ports, the suction tube supporting a suction nozzle; and the suction applying step comprises attaching a vacuum line to the suction nozzle for application of suction to the body organ through the applied suction ports.

24. The method of claim 23, further comprising the step of extending the vacuum line through one of the first and second incision.

25. The method of claim 3, wherein the shaft body comprises a suction lumen of the shaft body extending from a suction fitting at the shaft handle adapted to be coupled to a vacuum source to a distal lumen end opening, and the attaching step further comprises coupling the distal lumen end opening to the suction head to enable application of suction from the vacuum source through the suction lumen to tissue of the body organ contacted by the suction pad to engage the body organ.

26. The method of claim 25, wherein: the suction pad comprises first and second suction pods supported by the suction head fastener element to extend substantially in parallel and spaced apart from one another; the suction head comprises a spreading mechanism that selectively spreads the first and second suction pods apart; and the suction applying step comprises: applying suction through the suction lumen and the suction pods to grasp the organ tissue; and operating the spreading mechanism to spread the first and second suction pods apart to stretch the organ tissue between the first and second suction pods when suction is applied therethrough to the organ tissue to stabilize the organ tissue between the first and second suction pods to facilitate performing the medical procedure upon the body organ employing the second incision.

27. A method of performing a medical procedure on a body accesses through first and second incisions into a body cavity comprising:
providing an elongated shaft having a shaft body extending between a proximal shaft handle and a shaft body distal end, the shaft body distal end supporting a shaft fastener element, providing a suction head having a suction pad adapted to be coupled to a source of suction to engage the body organ through the application of suction to the body organ and a suction head fastener element adapted to be attached to or detached from the shaft fastener element;
advancing the elongated shaft through the first incision to dispose the shaft body distal end within the body cavity or inserted through both the first and second incision to dispose the shaft body distal end outside the body adjacent the second incision while the shaft handle is disposed outside the body adjacent the first incision;
attaching the suction head fastener element to the shaft fastener element to form a suction-assisted tissue-engaging device; positioning the suction pad of the suction head against the body organ;
applying suction through the suction pad to engage the body organ;
performing the medical procedure on the body organ via the second incision; and
further comprising upon completion of the medical procedure: discontinuing application of suction; advancing the coupled together shaft body distal end and suction head of the suction-assisted tissue-engaging device through the second incision from the body cavity outside the body; detaching the suction head fastener element from the shaft fastener element; and removing the shaft body from the chest cavity through the first incision.

28. The method of claim 27, further comprising coupling a blunting element to the shaft body distal end prior to removing the shaft body through the first incision.

29. A method of performing a medical procedure on a body organ, accessed through first and second incisions into a body cavity comprising:
providing a first portion and a second portion of a suction-assisted tissue-engaging device;
advancing the first portion of the suction-assisted tissue-engaging device through the first incision into the body cavity and from the first incision through the second incision outside the body;
coupling the second portion of the suction-assisted tissue-engaging device to the first portion of the suction-assisted tissue-engaging device outside the body;
retracting the second portion through the second incision into the body cavity;
positioning the second portion of the suction-assisted tissue-engaging device against the body organ;
applying suction through the second portion of the suction-assisted tissue-engaging device to engage the body organ; and,
performing the medical procedure on the body organ via the second incision.

30. The method of claim 29, further comprising upon completion of the medical procedure:
discontinuing application of suction; repositioning the second portion of the suction-assisted tissue-engaging device from the body organ through the second incision outside the body;
uncoupling the second portion of the suction-assisted tissue-engaging device from the first portion of the suction-assisted tissue-engaging device via the second incision; and
removing the first portion of the suction-assisted tissue-engaging device from the chest cavity through the first incision.

31. The method of claim 30, wherein the positioning step further comprises: orienting the first portion through the first incision into an operative vector in 3-D space for engagement of the second portion with the body organ; and
rigidly maintaining the operative vector to enable performance of the medical procedure on the body organ.

32. The method of claim 29, wherein the positioning step further comprises: orienting the first portion through the first incision into an operative vector in 3-D space for engagement of the second portion with the body organ; and
rigidly maintaining the operative vector to enable performance of the medical procedure on the body organ.

33. The method of claim 29, wherein:

the first portion comprises an elongated shaft having a shaft body extending between a proximal shaft handle and a shaft body distal end, the shaft body distal end supporting a shaft fastener element, shaft body adapted to be selectively inserted through the first incision to dispose the shaft body distal end within the body cavity or inserted through both the first and second incision to dispose the shaft body distal end outside the body adjacent the second incision while the shaft handle is disposed outside the body adjacent the first incision; and the second portion comprises a suction head having a suction pad adapted to be coupled to a source of suction to engage the body organ through the application of suction to the body organ and a suction head fastener element adapted to be attached to or detached from the shaft fastener element.

* * * * *

UNITED STATES PATENT AND TRADEMARK OFFICE
CERTIFICATE OF CORRECTION

| | | |
|---|---|---|
| PATENT NO. | : 7,494,460 B2 | |
| APPLICATION NO. | : 10/675815 | |
| DATED | : February 24, 2009 | |
| INVENTOR(S) | : Philip J. Haarstad et al. | |

It is certified that error appears in the above-identified patent and that said Letters Patent is hereby corrected as shown below:

Title page, item (75) Inventors: William J. Steinberg .... should be .... William A. Steinberg In Column 25, line 50: Amend claim 56 .... body accesses through.... should be .... body organ, accessed through...

Signed and Sealed this
First Day of May, 2012

David J. Kappos
*Director of the United States Patent and Trademark Office*